US008119598B2

(12) United States Patent
Keeley et al.

(10) Patent No.: US 8,119,598 B2
(45) Date of Patent: Feb. 21, 2012

(54) SYNTHETIC PEPTIDE MATERIALS FOR JOINT RECONSTRUCTION, REPAIR AND CUSHIONING

(75) Inventors: Fred Keeley, Toronto (CA); Aser Rothstein, Guelph (CA); Steven Rothstein, Guelph (CA); Kimberly Woodhouse, Toronto (CA)

(73) Assignees: Hospital For Sick Children, Toronto, Ontario (CA); Elastin Specialties, Inc., Guelph, Ontario (CA)

( * ) Notice: Subject to any disclaimer, the term of this patent is extended or adjusted under 35 U.S.C. 154(b) by 577 days.

(21) Appl. No.: 12/149,645

(22) Filed: May 6, 2008

(65) Prior Publication Data
US 2009/0075868 A1 Mar. 19, 2009

Related U.S. Application Data

(60) Provisional application No. 60/924,366, filed on May 10, 2007.

(51) Int. Cl.
*A61K 38/00* (2006.01)
*A61K 38/16* (2006.01)
*A61K 38/17* (2006.01)
*C07K 14/00* (2006.01)

(52) U.S. Cl. ...... 514/17.1; 514/21.2; 530/353; 530/355; 530/402

(58) Field of Classification Search .................. None
See application file for complete search history.

(56) References Cited

U.S. PATENT DOCUMENTS

| 4,132,746 A | 1/1979 | Urry et al. |
| 4,179,333 A | 12/1979 | Braeumer et al. |
| 4,327,078 A | 4/1982 | Charlet et al. |
| 4,419,288 A | 12/1983 | Cioca |
| 4,474,763 A | 10/1984 | Lubowe |
| 4,474,851 A | 10/1984 | Urry |
| 4,500,700 A | 2/1985 | Urry |
| 4,589,882 A | 5/1986 | Urry |
| 4,659,740 A | 4/1987 | Usher |
| 4,776,853 A | 10/1988 | Klement et al. |
| 4,783,523 A | 11/1988 | Urry et al. |
| 4,870,055 A | 9/1989 | Urry et al. |
| 4,960,423 A | 10/1990 | Smith |
| 4,963,656 A | 10/1990 | Mitani |
| 4,979,959 A | 12/1990 | Guire |
| 5,223,420 A | 6/1993 | Rabaud et al. |
| 5,243,038 A | 9/1993 | Ferrari et al. |
| 5,250,516 A | 10/1993 | Urry |
| 5,336,256 A | 8/1994 | Urry |
| 5,416,074 A | 5/1995 | Rabaud et al. |
| 5,519,004 A | 5/1996 | Urry |
| 5,527,610 A | 6/1996 | Urry |
| 5,879,396 A | 3/1999 | Walston et al. |
| 5,969,106 A | 10/1999 | Rothstein et al. |
| 6,489,446 B1* | 12/2002 | Rothstein et al. ............. 530/353 |
| 6,765,086 B2 | 7/2004 | Rothstein et al. |
| 7,001,328 B1* | 2/2006 | Barofsky et al. ................. 600/36 |
| 7,060,100 B2 | 6/2006 | Ferree et al. |
| 2001/0051832 A1* | 12/2001 | Bakker et al. .............. 623/23.58 |
| 2005/0196427 A1 | 9/2005 | Tierrell et al. |
| 2006/0178743 A1 | 8/2006 | Carter |

FOREIGN PATENT DOCUMENTS

| DE | 39 42 580 | 6/1991 |
| EP | 0 329 622 A | 8/1989 |
| WO | WO-86/05097 | 9/1986 |
| WO | WO-88/03533 | 5/1988 |
| WO | WO-90/05177 | 5/1990 |
| WO | WO-91/16919 | 11/1991 |
| WO | WO-92/09695 | 6/1992 |
| WO | WO-94/14958 | 7/1994 |
| WO | WO-95/244788 | 9/1995 |

OTHER PUBLICATIONS

Gross et al., Z Naturforsch C, 2003, vol. 58(11-12):873-878.*
Gray et al., "Molecular Model for Elastin Structure and Function," *Nature*, vol. 246, pp. 461-466, Dec. 1973.
Foster et al., "Isolation and Amino Acid Sequences of Tropoelastin Peptides," *The Journal of Biological Chemistry*, vol. 248, No. 8, pp. 2876-2879, 1973.
International Search Report issued on Jan. 20, 2009 in application No. PCT/US2008/005790 (corresponding to US 2009/0075868).
International Search Report issued on Jan. 16, 2001 in application No. PCT/US00/17829 (corresponding to US 6,765,086).
International Search Report issued on Mar. 18, 1998 in application No. PCT/CA97/00560 (corresponding to US 5,969,106).
Bedell-Hogan, et al.; "Oxidation, Cross-Linking and Insolubilization of Recombinant Tropoelastin by Purified Lysyl Oxidase"; *JBC*, May 15, 1993, pp. 10345-10350, vol. 268.
Bressen et al.; "Relevance of Aggregation Properties Tropoelastin to the Assembly and Structure of Elastic Fibers"; *J. Ultrastruct. Mol. Struct.*, 1986, pp. 209-216.
Cappello; "Protein Engineering for Biomaterials Applications"; *Curr. Opinion Struct. Biol.* 2:582-86 (1992).
Dutoya, et al.; "Unexpected Original Property of Elastin Derived Proteins: Spontaneous Tight Coupling with Natural and Synthesis Polymer"; Biomaterials 19 (1998) pp. 147-155. Hamodrakas, et al.; "Structural and Functional Features of *Drosophila chorion* proteins s36 and s38 from Analysis of Primary Structure and Infrared Spectroscopy"; Oct. 1989, pp. 307-313, vol. 11.
Hinek, et al.; "67-Kd Elastin-binding Protein in a Protective "Companion" of Extracellular Insoluable Elastin and Intracellular Topoelatin"; Jul. 1994, pp. 563-574.
Hinek; "Nature and the Multiple Functions of the 67-kD Elastin/Laminin Binding Protein"; Cell Adhesion & Comm.; 2:185-93 (1994).
Indik et al.; "Alternative Splicing of Human Elastin mRNA Indicated by Sequence Analysis of Cloned Genomic and Complementary DNA"; Aug. 1987, pp. 5680-5684, vol. 84.
Indik, et al.; "Production of Recombinant Human Tropoelastin: Characterization and Demonstration of Immunologic and Chemotactic Activity"; Jul. 1990, pp. 80-86, vol. 280.

(Continued)

*Primary Examiner* — Elizabeth C Kemmerer
*Assistant Examiner* — Xiaozhen Xie
(74) *Attorney, Agent, or Firm* — Foley & Lardner LLP

(57) ABSTRACT

In joint reconstruction, repair and cushioning applications, a synthetic polypeptide material is useful that contains crosslinked polypeptides that are modeled on human elastin or other fibrous proteins. The polypeptides comprise at least three consecutive beta-sheet/beta-turn structures and at least one amino acid residue that participates in cross-linking.

24 Claims, 11 Drawing Sheets

OTHER PUBLICATIONS

Robson, et al.; "Characterization of Lamprin, an Unusual Matrix Protein form Lamprey Cartilage"; *Journal of Biological Chemistry*, Jan. 15, 1993, pp. 1440-1447, vol. 266.
Robson, et al.; J. Biol Chem.; vol. 268, pp. 1440-1447.
Simmons, et al.; "Molecular Orientation and Two-Component Nature of Crystalline Fraction of Spider Dragline Silk," *Science*, vol. 271, Jan. 5, 1996, pp. 84-87.
Tamburro, et al.; "On the Structure and Elasticity of Elastin"; Advances in Life Sciences; pp. 115-127 (1990).
Bellingham et al., *Biopolymers*, 70:445-455 (2003).
Elvin et al., *Nature*, 437:999-1002 (2005).
Urry et al., *Biochemistry*, 15:4083-4089 (1976).
Prince et al., *Biochemistry*, 34:10879-10885 (1985).
Mecham et al., *CIBA Found. Symp.*, 192:172-184 (1995).
Volpin, *Adv. Exp. Med. Biol.*, 79:119-128 (1977).
Kagan et al., *JBC*, 255:3656 (1980).
Lee et al., *Biomacromolecules*, 2(1): 170-179 (2001).
Kimura et al., *J. Muscle Res. Cell. Motil.*, 13:39-47 (1992).
Grosso et al., *Matrix*, 13:157-164 (1993).
Martin et al., *Gene*, 154:159-166 (1995).
Abraham et al., *J. Biol. Chem.*, 253:7993-7995 (1978).
Urry et al., *J. Biomed. Mater. Res.*, 16:11-16 (1982).
Urry, *J. Protein Chem.*, 7:1-34 (1988).

* cited by examiner

FIG. 1A

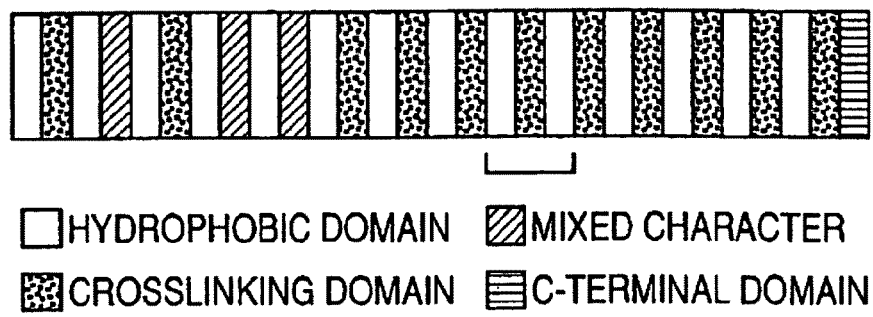

☐ HYDROPHOBIC DOMAIN   ▨ MIXED CHARACTER
▧ CROSSLINKING DOMAIN  ☰ C-TERMINAL DOMAIN

FIG. 1B

```
  1           11          21          31          41          51
GGVPGAIPGG  VPGGVFYPGA  GLGALGGGAL  GPGGKPLKPV  PGGLAGAGLG  AGLGAFPAVT
FPGALVPGGV  ADAAAAYKAA  KAGAGLGGVP  GVGGLGVSAG  AVVPQPGAGV  KPGKVPGVGL
PGVYPGGVLP  GARFPGVGVL  PGVPTGAGVK  PKAPGVGGAF  AGIPGVGPFG  GPQPGVPLGY
PIKAPKLPGG  YGLPYTTGKL  PYGYGPGGVA  GAAGKAGYPT  GTGVGPQAAA  AAAAKAAAKF
GAGAAGVLPG  VGGAGVPGVP  GAIPGIGGIA  GVGTPAAAAA  AAAAAKAAKY  GAAAGLVPGG
PGFGPGVVGV  PGAGVPGVGV  PGAGIPVVPG  AGIPGAAVPG  VVSPEAAAKA  AAKAAKYGAR
PGVGVGGIPT  YGVGAGGFPG  FGVGVGGIPG  VAGVPSVGGV  PGVGGVPGVG  ISPFAQAAAA
AKAAKYGVGT  PAAAAAKAAA  KAAQFGLVPG  VGVAPGVGVA  PGVGVAPGVG  LAPGVGVAPG
VGVAPGVGVA  PGIGPGGVAA  AAKSAAKVAA  KAQLRAAAGL  GAGIPGLGVG  VGVPGLGVGA
GVPGLGVGAG  VPGFGAGADE  GVRRSLSPEL  REGDPSSSQH  LPSTPSSPRV  PGALAAAKAA
KYGAAVPGVL  GGLGALGGVG  IPGGVVGAG   PAAAAAAAKAA  AKAAQFGLVG  AAGLGGLGVG
GLGVPGVGGL  GGIPPAAAAK  AAKYGAAGL   GGVLGGAGQFP  LGGVAARPGF  GLSPIFPGGA
CLGKACGRKR  K
```

FIG. 1C

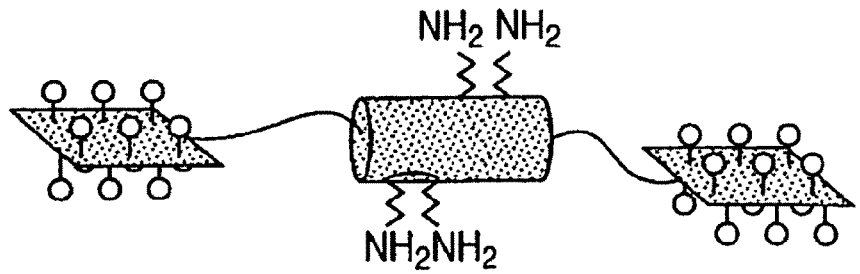

FIGURE 3C (MFU-2)

| | | | |
|---|---|---|---|
| FPGFGVGVGGI | PGVAGVPGVG | GVPGVGGVPG | VGISPEAQAA |
| AAAKAAKYGV | GTPAAAAAKA | AAKAAQFGLV | PGVGVAPGVG |
| VAPGVGVAPG | VGLAPGVGVA | PGVGVAPGVG | VAPAIGPEAQ |
| AAAAAKAAKY | GVGTPAAAAA | KAAAKAAQFG | LVPGVGVAPG |
| VGVAPGVGVA | PGVGLAPGVG | VAPGVGVAPG | VGVAPAIGP |

FIGURE 4A (MFU-3)

| | | | |
|---|---|---|---|
| PGFGVGVGGI | PGVAGVPGVG | GVPGVGGVPG | VGISPEAQAA |
| AAAKAAKYGV | GTPAAAAAKA | AAKAAQFGLV | PGVGVAPGVG |
| VAPGVGVAPG | VGLAPGVGVA | PGVGVAPGVG | VAPAIGP |

FIGURE 4B (MFU-4)

| | | | |
|---|---|---|---|
| FPGFGVGVGG | IPGVAGVPGV | GGVPGVGGVP | GVGISPEAQA |
| AAAAKAAKYG | VGTPAAAAAK | AAAKAAQFGL | VPGVGVAPGV |
| GVAPGVGVAP | GVGLAPGVGV | APGVGVAPGV | GVAPAIGP |

FIGURE 4C (MFU-5)

| | | | |
|---|---|---|---|
| PGFGVGVGGI | PGVAGVPGVG | GVPGVGGVPG | VGISPEAQAA |
| AAAKAAKYGV | GTPAAAAAKA | AAKAAQFGLV | PGVGVAPGVG |
| VAPGVGVAPG | VGLAPGVGVA | PGVGVAPGVG | VAPAIGPEAQ |
| AAAAAKAAKY | GVGTPAAAAA | KAAAKAAQFG | LVPGVGVAPG |
| VGVAPGVGVA | PGVGLAPGVG | VAPGVGVAPG | VGVAPAIGP |

FIGURE 5A (MFU-6)

FPGFGVGVGGIPGVAGVPGVGGVPGVGGVPGVGISP
EAQAAAAAKAAKYGVTPAAAAAKAAAKAAQFGLVPGVGVAPGVGVAPGVGVAPG
VGLAPGVGVAPGVGVAPGVGVAPAIGP
EAQAAAAAKAAKYGVTPAAAAAKAAAKAAQFGLVPGVGVAPGVGVAPGVGVAPG
VGLAPGVGVAPGVGVAPGVGVAPAIGP
EAQAAAAAKAAKYGVTPAAAAAKAAAKAAQFGLVPGVGVAPGVGVAPGVGVAPG
VGLAPGVGVAPGVGVAPGVGVAPAIGP
EAQAAAAAKAAKYGVTPAAAAAKAAAKAAQFGLVPGVGVAPGVGVAPGVGVAPG
VGLAPGVGVAPGVGVAPGVGVAPAIGP

FIGURE 5B (MFU-7)

PGFGVGVGGIPGVAGVPGVGGVPGVGGVPGVGISP
EAQAAAAAKAAKYGVTPAAAAAKAAAKAAQFGLVPGVGVAPGVGVAPGVGVAPG
VGLAPGVGVAPGVGVAPGVGVAPAIGP
EAQAAAAAKAAKYGVTPAAAAAKAAAKAAQFGLVPGVGVAPGVGVAPGVGVAPG
VGLAPGVGVAPGVGVAPGVGVAPAIGP
EAQAAAAAKAAKYGVTPAAAAAKAAAKAAQFGLVPGVGVAPGVGVAPGVGVAPG
VGLAPGVGVAPGVGVAPGVGVAPAIGP
EAQAAAAAKAAKYGVTPAAAAAKAAAKAAQFGLVPGVGVAPGVGVAPGVGVAPG
VGLAPGVGVAPGVGVAPGVGVAPAIGP

SYNTHETIC PEPTIDE MATERIALS FOR JOINT RECONSTRUCTION, REPAIR AND CUSHIONING

CROSS-REFERENCE TO RELATED APPLICATIONS

This application claims priority under 35 U.S.C. §119(e) to U.S. Provisional Patent Application No. 60/924,366, filed May 10, 2007, the entire contents of which are incorporated herein by reference in their entirety for any and all purposes.

FIELD OF THE INVENTION

The present invention relates to synthetic peptide materials useful, for example, in joint reconstruction, repair and cushioning applications, and related methods. In some embodiments, the materials comprise self-aligning and self-assembling polypeptides modeled on human elastin, or other fibrous proteins.

BACKGROUND OF THE INVENTION

Loss of cushioning between joint surfaces is a basis of several significant orthopedic problems. Damage to contact surfaces in articular joints such as hips, shoulders, knees and digits as a consequence of arthritic conditions also results in debilitating disease which may require surgical intervention in the form of joint replacement with synthetic materials. Loss of cushioning between joint surfaces may also be the result of damage to tissues, such as ligaments, which stabilize joints, causing misalignment of articulating surfaces and resulting in abnormal wear. Such misalignment traditionally may require surgical intervention to stabilize the joint and re-establish normal joint articulation. Degeneration of intervertebral disc tissues results in chronic, debilitating back pain, calcification and rigidification of the spine and significant neurological consequences not only in humans but also in domestic animals, particularly dogs. Surgical alternatives include prosthetic devices to replace the intervertebral disc, some of which consist of metal/rubber artificial discs or synthetic hydrogels. For examples, see U.S. Pat. Nos. 5,879,396; 7,060,100; and 5,879,396.

Elastin, a natural structural protein, has received considerable attention for potential use in prostheses, such as vascular prosthesis, both in soluble forms for coating non-biological prostheses, and in solid forms to produce biologically-derived prostheses. Elastin has structural properties which make it suitable for use in prosthesis and it provides a biocompatible, non-thrombogenic surface for cell infiltration. It is a durable, extremely stable, and highly insoluble extracellular matrix protein which imparts the properties of extensibility and elastic recoil to tissues in which it is found, including large blood vessels, elastic ligaments, lung parenchyma, and skin.

Large arteries are a good source of elastin. Because human arteries are not available in quantity, animal arteries have been the primary source for elastin. However, arterial elastin is a highly insoluble matrix; therefore, soluble elastin-derived material is generated by treating the insoluble protein with acid or alkali, producing hydrolyzates such as alpha- and kappa-elastin. These are relatively undefined mixtures of peptides of mixed sizes. Thus, sources for large quantities of natural elastin are not readily available.

In attempts to develop biocompatible materials, soluble animal elastin materials have been used to coat non-biological prosthetic materials, usually with fixation by chemical cross-linking agents. For example, U.S. Pat. No. 4,960,423 (Smith) is directed to a synthetic vascular prosthesis coated with a water-soluble peptide derived from animal elastin.

U.S. Pat. No. 5,416,074 (Rabaud) is directed to a composition comprising elastin or a solubilized elastin peptide and another connective tissue protein, such as fibrin. The solubilized elastin peptide has a molecular weight of greater than 10,000.

U.S. Pat. No. 4,474,851 (Urry) is directed to an elastomeric composite material comprising an artificial core fiber, such as Dacron, and a polypeptide comprising repeating tetrapeptide or pentapeptide units. The units are derived from units observed to be repeated in the tropoelastin molecule, Val-Pro-Gly-Val-Gly (VPGVG; SEQ ID NO:6) and Val-Pro-Gly-Gly (VPGG; SEQ ID NO:7). The polypeptide comprises a series of beta-turns and is proposed to have a beta-coil structure. The polypeptide provides elastomeric properties to the composite material, but has little structural strength or integrity. The artificial core fiber provides these latter properties to the composite material.

U.S. Pat. No. 4,979,959 (Guire) is directed to a method of improving the biocompatibility of solid biomaterials by coating them with biocompatible agents and chemically linking the biocompatible agents to the surface via a photochemical reaction.

Elastin-based materials also have been used to produce solid materials from which prostheses can be manufactured. These include soluble animal elastin co-aggregated with other proteins such as collagen, fibrin, fibronectin and laminin, to produce gel-like materials, and polymerized materials derived from short hydrophobic sequences of human elastin (such as PGVGVA; SEQ ID NO:5). In some cases, these synthetic peptides also include short alanine-rich sequences containing lysine residues, allowing cross-linking between the elastin-like peptides or to other proteins such as collagen. Both elastin and collagen contain crosslinks derived from lysine. For example. U.S. Pat. No. 5,223,420 (Rabaud) is directed to an elastin-based product comprising an adduct containing elastin and at least one other protein, such as fibrin.

U.S. Pat. No. 4,589,882 (Urry) is directed to an artificial elastomeric copolymer comprising an elastomeric component of repeating units of tetrapeptides and pentapeptides and a crosslinking component which may comprise amino acid residues. The repeating units are derived from elastin. U.S. Pat. No. 4,132,746 (Urry) is directed to a synthetic, insoluble, crosslinked polypentapeptide. The pentapeptide is the VPGVG (SEQ ID NO:6) peptide present in tropoelastin. See also U.S. Pat. Nos. 4,500,700; 4,870,055, and 5,250,516 (all to Urry) for other materials derived from this peptide. The polypeptides described in these patents comprise a series of beta-turns and are proposed to have a beta-coil structure.

Animal arteries also have been stripped of extraneous material, leaving largely a matrix of elastin and collagen in tubular form that can be used for blood vessel replacement. For example, U.S. Pat. No. 4,776,853 (Klement) is directed towards a process for preparing an implantable biological material from suitable donor tissue.

U.S. Pat. Nos. 5,969,106; 6,489,446 and 6,765,086 describe polypeptides modeled on elastin and other naturally occurring fibrous proteins for use in a variety of applications, including as prosthesis (including vascular prosthesis), and in cosmetics.

There remains a need for synthetic polypeptide materials suitable for joint reconstruction, repair and cushioning that exhibit properties of extensibility, resilience and compressibility, yet are non-immunogenic and non-thrombogenic.

SUMMARY OF THE INVENTION

In accordance with one embodiment, there is provided a synthetic polypeptide material for join reconstruction, repair, and/or cushioning comprising crosslinked polypeptides, wherein (A) each polypeptide comprises at least three consecutive beta-sheet/beta-turn structures and at least one crosslinking amino acid residue that participates in cross-linking, wherein the crosslinking residue is distinct from the beta-sheet/beta-turn structures, and (B) each polypeptide is between 150 and 500 amino acids in length and wherein the material is a solid or liquid suitable for insertion into a joint or into a site near a joint. In particular aspects, each beta-sheet structure may comprise from 3 to about 7 amino acid residues. In some embodiments, the amino acid sequences of the crosslinked polypeptides are the same; while in other embodiments the amino acid sequences of the crosslinked polypeptides are different.

In some embodiments, the material further comprises a reinforcing material, such as an animal material, a synthetic material or metal. In other embodiments, the material further comprises a non-protein hydrophilic polymer.

In some embodiments, the material further comprises glycosaminoglycan moieties, such as hyaluronan moieties. In some embodiments, the material comprises a mixture of crosslinked polypeptides and glycosaminoglycan moieties. In other embodiments the crosslinked polypeptides are covalently linked to the glycosaminoglycan moieties.

In some embodiments, the material is a solid, and may be in the form of pads, sheets and ligament-like structures. In other embodiments, the material is a liquid, such as a solution or suspension that further comprises a pharmaceutically acceptable carrier suitable for injection.

In accordance with another embodiment, there is provided a method for the reconstruction, repair or cushioning of a joint comprising inserting into the joint, or into a site near the joint, a synthetic polypeptide material comprising crosslinked polypeptides, wherein (A) each polypeptide comprises at least three consecutive beta-sheet/beta-turn structures and at least one crosslinking amino acid residue that participates in cross-linking, wherein the crosslinking residue is distinct from the beta-sheet/beta-turn structures, and (B) each polypeptide is between 150 and 500 amino acids in length.

BRIEF DESCRIPTION OF THE DRAWINGS

FIG. 3C shows the amino acid sequence of MFU-2 (SEQ ID NO:2).

FIGS. 4A, 4B and 4C show the amino acid sequences of MFU-3 (SEQ ID NO: 8), MFU-4 (SEQ ID NO: 9), and MFU-5 (SEQ ID NO: 10), respectively.

FIGS. 5A and 5B show the amino acid sequences of MFU-6 (SEQ ID NO: 11) and MFU-7 (SEQ ID NO: 12), respectively. The sequences include a seven fold PGVGVA (SEQ ID NO:5) repeat. Crosslinking domains KAAK (SEQ ID NO: 3) and KAAAK (SEQ ID NO:4) are underlined.

FIG. 6A shows a top view of the pad approximately 3 mm in diameter and 3 mm in thickness prepared by the centrifugation methods outlined in Example 1. FIG. 6B shows a side view of the pad approximately 3 mm in diameter and 3 mm in thickness prepared by the centrifugation methods outlined in Example 1.

DETAILED DESCRIPTION

Figure 1:
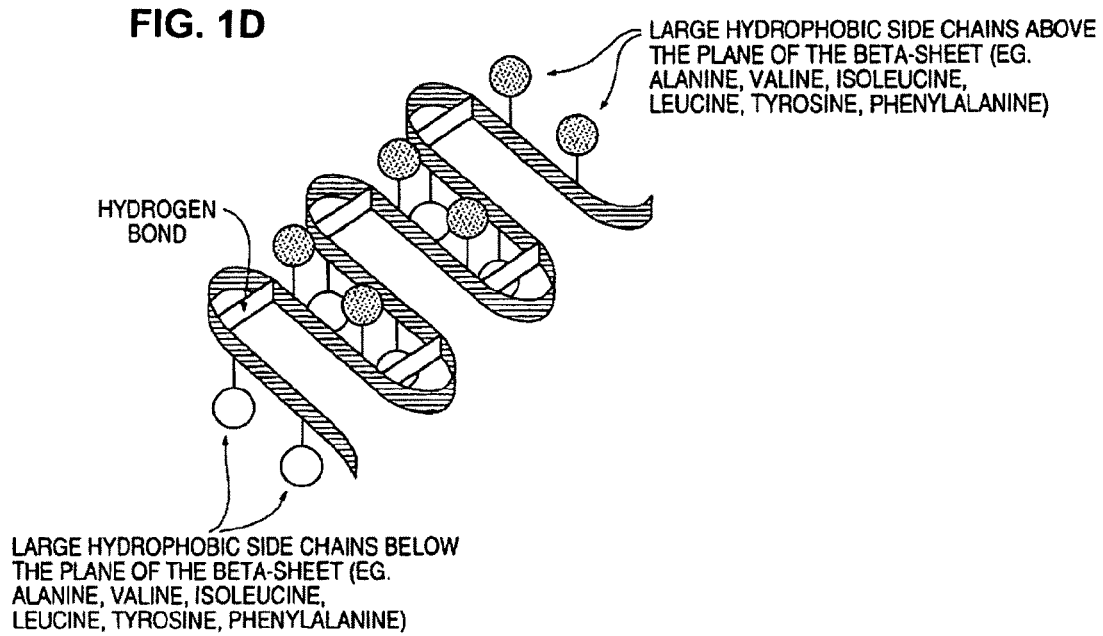
FIG. 1A shows the domain structure of human elastin.
FIG. 1B shows the amino acid sequence of human elastin (SEQ ID NO:1), without the signal peptide. The underlined amino acid residues comprise the polypeptide named MFU-1.
FIG. 1C is a cartoon representation of the hydrophobic and crosslinking domains corresponding to the expressed exons in MFU-1.
FIG. 1D is a schematic diagram of a peptide with beta-sheet/beta-turn structures.

Described herein are synthetic polypeptide materials that are useful, for example, in joint reconstruction, repair and cushioning applications.

The singular forms "a," "an," and "the" include plural reference unless the context clearly dictates otherwise.

As used herein, the term "synthetic" polypeptide material specifies that the material is not a naturally occurring material. The polypeptides comprised in the synthetic polypeptide material described herein are typically obtained by recombinant methods, but may be obtained by other means, including chemical synthesis or cleavage of larger polypeptides or proteins.

As used herein, the term "joint" refers to any joint in a human or other animal, including hips, knees, elbows, shoulders, digits and other articulating joints, as well as intervertebral discs and other similar sites.

As used herein, the term "joint reconstruction or repair" includes any process used for replacement or repair (e.g., reinforcement) of ligament or cartilage structures that normally line or stabilize joint structures.

As used herein, the term "joint cushion" includes any material that is implanted or injected into the body to provide cushioning at a joint. For example, a joint cushion may cover a terminus of a bone and allow the joint to move easily. In some circumstances, a joint cushion functions similar to cartilage as a rubbery, fibrous, dense, connective material. As appreciated by one of skill in the art, cartilage usually is found between bones and permits smooth movement of joints. The term "joint cushion" also includes a material which, when injected into a joint space, such as, for example, the area of an intervertebral disc, provides a resilient material for separation of bony surfaces.

While natural elastin has been understood to confer extensibility properties on the tissues in which it is found, the present invention relates in part to the discovery that polypeptides modeled on elastin or other fibrous proteins exhibit advantageous properties with respect to resilience in resistance to compressive forces (e.g., compressibility). Elastin is a major component of intervertebral disc tissues, which act as a shock absorber between the vertebrae as well as providing for flexibility of the spine, and large pads of elastin-like materials are known to provide cushions in the feet of massive animals, such as elephants. Furthermore, elastin is a major component of several cartilaginous tissues, including auricular, bronchial and laryngeal cartilage. The compressibility of elastin may make it particularly suitable for these natural applications. Described herein are polypeptides modeled on elastin or other fibrous proteins that exhibit compressibility properties that are particularly advantageous for applications including joint reconstruction, joint repair and joint cushioning applications.

In some embodiments, the synthetic polypeptide materials comprise polypeptides that are modeled on elastin, including human elastin. In other embodiments, the materials comprise polypeptides that are modeled on other fibrous proteins, or that are modeled on combinations of one or more of elastin and/or other fibrous proteins. In still other embodiments the materials may comprise polypeptides in combination with other, non-protein materials such as hydrophilic polymers or glycosaminoglycan moieties, for example, hyaluronan moieties. Such combinations include both simple mixtures of components as well as materials comprising covalent linkages between components, such as materials comprising glycosaminoglycan moieties linked covalently to polypeptides through functional groups on the polypeptides, where the functional groups are normally present on the polypeptide, or are introduced into the polypeptide by methods known in the art.

In some embodiments, the synthetic polypeptide materials comprise crosslinked polypeptides, and are provided as cushions or other structures (such as sheets or pads) suitable for joint reconstruction, repair, or cushioning applications. In other embodiments, liquid soluble or suspended forms of the synthetic polypeptide materials are provided, and are suitable for injection, such as injection into tissue spaces such as the intervertebral disk space, where they provide cushioning between bony surfaces. In other embodiments, the synthetic polypeptide materials are provided as a ligament-like structure, suitable, for example, for surgical implantation to stabilize joints.

In some embodiments, the synthetic polypeptide materials exhibit properties such as elastic recoil, resistance to compression (e.g., compressibility, including resistance to repetitive compressive forces), resilience, and durability that make the materials particularly suitable for joint reconstruction, repair, or cushioning applications, such as use as cushions to alleviate joint wear and pain or as a plug material for the surgical repair of localized damage to articular joint surfaces. For example, in accordance with some embodiments, the synthetic polypeptide materials are useful as graft material to cushion joint surfaces, improve joint motion, and/or protect against further damage to the articulating surfaces of joints. The use of the synthetic polypeptide materials described herein in such applications could delay or prevent the requirement for wholesale joint replacement.

As exemplified below, the synthetic polypeptide materials can be made by polymerizing polypeptides from solution (e.g., via concentration or temperature) at polypeptide concentrations, solution temperatures and ionic solution strengths appropriate for the nature of the polypeptide(s) and the desired properties of the material.

In some embodiments, the synthetic polypeptide materials are fabricated into sheets or pads. These sheets or pads typically have a thickness of from about 1 to about 5 mm, but also may be of other thicknesses, such as from about 0.1 to about 1.0 mm, from about 1 to about 2 mm, from about 2 to about 5 mm, from about 1 to about 10 mm, or from about 5 to about 10 mm, depending on the intended application. Thus, the invention includes synthetic polypeptide materials fabricated into sheets or pads with a thickness of including from 1-5 mm, from 0.1-1.0 mm, from 1-2 mm, from 2-5 mm, from 1-10 mm, or from 5-10 mm, or any other thickness appropriate for the intended application.

To fabricate sheets or pads from coacervated polypeptides, the coacervate can be concentrated, such as by centrifugation or filtration techniques (Example 1), or foaming techniques can be used (Example 2). Those skilled in the art will recognize other suitable ways to obtain the synthetic polypeptide materials described herein.

In some embodiments, the synthetic polypeptide materials are provided in liquid soluble or suspended forms, such as dissolved or suspended in pharmaceutically acceptable carriers for injection. For example, polypeptides may be dissolved in phosphate-buffered saline or other physiologically suitable solutions at concentrations such that they remain soluble at temperatures below normal in vivo temperatures (e.g., below body temperature, such as at room temperature or at about 37°). In some embodiments, the polypeptides undergo coacervation (e.g., self-assembly and precipitation into a solid polymeric matrix) upon exposure to higher temperatures, such as upon in vivo injection and exposure to normal in vivo temperatures (e.g., body temperatures). In accordance with this embodiment, a solid matrix of the synthetic polypeptide materials is formed in situ, in the vicinity of the injection site. Related to this embodiment is a method of effecting joint repair, reconstruction and/or cushioning that comprises injecting soluble or suspended forms of the synthetic polypeptide materials into a joint site in need of repair, reconstruction and/or cushioning. Advantageously, this embodiment permits repair, reconstruction and/or cushioning without requiring surgical insertion of a joint replacement material.

In accordance with some embodiments, the synthetic polypeptide materials are crosslinked. Crosslinking may, for example, stabilize the materials, and/or confer desired properties on the material, including compressibility. Exemplary crosslinking agents include (but are not be restricted to) glutaraldehyde, genipin, bis[sulfosuccinimidyl] suberate, methylglyoxyl, glyoxyl, pyrroloquinoline quinone and lysine-diisocyanate. Those skilled in the art will recognize that other crosslinking agents can be used. Crosslinking can be effected by any means known in the art. Illustrative crosslinking methods are set forth in the examples.

In some embodiments, the use of a specific crosslinking agent affects the physical properties of the synthetic polypeptide materials. Crosslinkers are generally chosen based on the following characteristics: chemical specificity, spacer arm length, water solubility, homofunctional or heterofunctional reactive groups, thermoreactive or photoreactive groups, cleavability of crosslinker, and the ability to tag the crosslinker. The choice of crosslinker may affect the characteristics of the material. For example, crosslinking agents with multiple reactive sites, or that are capable of self-polymerization to increase their effective spacer arm length, will generally lead to a more rigid material than will shorter crosslinking agents with more limited spacer arm length. Crosslinking agents with different spacer arm lengths may be suitable for different materials, for example, if steric properties of the polypeptides affect the distance between potential crosslinking sites. Crosslinking agents also may be selected for their effect on the compressibility of the resulting material, as illustrated in the examples.

In some embodiments, crosslinking is effected simultaneously with coacervation, such as by adding a crosslinking agent to the material during coacervation. In other embodiments, crosslinking is effected subsequent to coacervation, such as by adding a crosslinking agent to the material after coacervation. Once the crosslinker is added, crosslinkages generally form and mature over a period of time, such as for example, over several hours, such as from one to five hours. In other embodiments, crosslinking is effected after the material is formed, such as by adding a crosslinking agent to the material after coacervation and concentration, using, for example, glutaraldehyde vapor as a crosslinking agent.

In some embodiments, the identity of the polypeptide(s) affects the physical properties of the synthetic polypeptide materials. For example, materials manufactured from polypeptides modeled on elastin have useful compressive physical properties (e.g., compressibility) that are particularly suited to joint reconstruction, repair and cushioning applications. In another embodiment, composite materials manufactured from polypeptides modeled on elastin and hydrophilic polymers, such as hyaluronic acid and other glycosaminoglycans, exhibit advantageous swelling and mechanical properties useful for joint reconstruction, repair and cushioning applications. In further embodiments, materials with different tensile physical properties (e.g., elastic modulus/compressibility, extensibility, breaking load, and viscoelasticity) can be obtained by using polypeptides with modified amino acid sequences, and/or modified arrangements of hydrophobic and/or crosslinking domains, and/or by using different crosslinking methodologies, as illustrated in the examples below.

In accordance with the description provided herein, the skilled artisan can select appropriate polypeptide design, fabrication technology and crosslinking methodology to obtain synthetic polypeptide materials exhibiting physical properties that will optimize performance as reconstruction, repair or cushioning materials at various sites.

In some embodiments, the synthetic polypeptide material has an increased compressibility as compared to a comparable material made from elastin. For example, the synthetic polypeptide material may have a compressibility that is at least about 10% greater, at least about 20% greater, at least about 25% greater, at least about 30% greater, at least about 40% greater, at least about 50% greater (e.g., 1.5 times the compressibility), at least about 60% greater, at least about 70% greater, at least about 75% greater, at least about 80% greater, at least about 90% greater, at least about 95% greater, or at least about 100% greater (e.g., twice the compressibility) than a comparable material made from elastin, when determined by comparable methods, such as the methods illustrated in the examples for determining elastic modulus. In some embodiments, the synthetic polypeptide material has a compressibility that is about twice, about three times, about four times, about five times, about ten times, or more, than a comparable material made from elastin, when determined by comparable methods.

Polypeptides

As noted above, the synthetic polypeptide materials described herein comprise polypeptides modeled on human elastin and/or other naturally occurring fibrous proteins. While the discussion below often refers to human elastin as the exemplary parent protein, polypeptides modeled on other naturally occurring fibrous proteins are contemplated by the present invention, and can be made and used in manners analogous to those described for polypeptides modeled on human elastin. Examples of other such parent proteins include lamprin, spider silk protein, and resilin.

The phrase "parent protein" here denotes the protein on which a polypeptide of the invention is modeled. As used herein, the phrase "a polypeptide modeled on parent protein X" denotes a polypeptide that comprises a portion of the amino acid sequences of parent protein X, but does not include the full length sequence of the parent protein. For example, a polypeptide modeled on human elastin comprises a portion of the human tropoelastin amino acid sequence, but does not include the entire human tropoelastin amino acid sequence. A "naturally occurring fibrous protein" is any fibrous protein found in nature, where the phrase "fibrous protein" has the conventional meaning in the art. Thus, a fibrous protein is a protein that consists of polypeptide chains arranged in a matrix so as to form long fibers or sheets. See Lehninger, BIOCHEMISTRY 60 (1975). Examples of fibrous proteins include, but are not limited to, elastin, lamprin, resilin, and spider silk protein. Robson et al., J. Biol. Chem. 268: 1440-47 (1993), incorporated by reference herein in its entirety, discloses additional proteins on which polypeptides of the present invention may be modeled.

Amino acid sequence information is available for elastin (including human, mouse, rat, chicken, bovine and porcine elastin) and other fibrous extracellular matrix proteins, such as spider silks, lamprin, and resilin. Together with analyses of secondary and tertiary structures, this information has led to general theories concerning their mechanical properties and, in particular, mechanisms for their assembly into insoluble fibers. For example, the amino acid sequence of lamprin is known, and the secondary structure of this protein is believed to comprise a number of beta-sheet/beta-turn structures. Robson et al., supra.

Elastin is synthesized in vivo as a monomer called tropoelastin which, upon secretion from the cell, assembles into a branched polymeric network through the formation of covalent crosslinks called desmosines. Mecham et al., in CELL BIOLOGY OF EXTRACELLULAR MATRIX, 2D ED. (New York, 1991). Desmosine crosslinks are generated enzymatically through the action of lysyl oxidase. Each desmosine incorporates the side chains of four lysine residues, two from each of the polypeptide chains involved. Although the principles underlying the elastomeric properties of elastin remain a matter of debate, there is agreement that this unusual property is dependent on the strongly hydrophobic nature of the protein.

Tropoelastin consists predominantly of alternating hydrophobic and crosslinking domains. Indik et al., Proc. Nat'l Acad. Sci. USA 84: 5680-84 (1986). Crosslinking domains are usually rich in alanine (A), with the lysines (K) destined for involvement in crosslink formation present in KAAK (SEQ ID NO:3) and KAAAK (SEQ ID NO:4) spacings. The domains separating these crosslinking regions are strongly hydrophobic in character, and contain many tandemly repeated tri-, tetra-, penta- and hexa-peptide sequences. In human elastin the most striking of these is the sequence PGVGVA (SEQ ID NO: 5), repeated 7 times in exon 24. Indik at al., supra.

Structural studies on repeat hydrophobic sequences (e.g., hydrophobic domains) indicate an exclusively beta-sheet/beta turn structure. That is, they comprise beta-sheets with intervening beta-turns. Analogous beta-sheet/beta-turn structures also contribute to the structures of other self-aggregating, polymeric matrix proteins, including spider silks, lamprin, and silk moth chorion, all of which form stable fibers or matrices with high tensile strength. These structures have been proposed to be crucial for the ability of these proteins to self-assemble. Robson et al., supra.

There is evidence that the periodically spaced hydrophobic domains direct the assembly of tropoelastin into higher order structures. Tropoelastin, as well as solubilized fragments of elastin (i.e., kappa-elastin and alpha-elastin), and synthetic peptides corresponding to the hydrophobic repeat sequences can all undergo coacervation, a process in which hydrophobic interactions between polypeptide chains result in the formation of oligomeric, fibrillar structures. This self-aggregation is not random: the hydrophobic domains facilitate the alignment of tropoelastin monomers for crosslinking into the fibrillar elastic matrix. Robson et al., supra; Bressan et al., J. Ultrastr. & Mol. Struct. Res. 94: 209-16 (1986); Bellingham et al., Biopolymers 70: 445-55 (2003).

Human elastin consists for most of its length of alternating crosslinking domains and hydrophobic domains. The crosslinking domains consist mainly of lysine (K) and alanine (A) residues in KAAK (SEQ ID NO:3) and KAAAK (SEQ ID NO:4) sequences, wherein the lysine residues are in a suitable conformation for oxidative deamination by lysyl oxidase and subsequent formation of the covalent desmosine crosslinks. Indik et al., supra. The hydrophobic domains are rich in hydrophobic pentapeptide, hexapeptide and other repeat sequences believed to be in beta-sheet/beta-turn structures. Tamburro et al., ADVANCES IN LIFE SCIENCES 115-27 (1990). These hydrophobic regions are believed to be important to elastin's physical properties of extensibility and elastic recoil, and to the ability of tropoelastin (the monomeric precursor of elastin) to self-aggregate into fibriliar structures. Robson et al., supra; Tamburro et al., supra. Other proteins capable of self-aggregation and self-alignment into stable fibriliar matrices, including eggshell chorion proteins of insects, spider dragline silk, and lamprin from lamprey cartilage, all possess similar regions of hydrophobic repeat peptides with beta-sheet/beta-turn structures. Hamodrakas el al., Int. J. Biol. Macromol. 11: 307-13 (1989); Simmons et al., Science 271: 84-87 (1996); Robson et al., supra.

Polypeptides useful in accordance with the invention are modeled on elastin and other fibrous proteins, such as spider silk, lamprin, and resilin, and comprise the number and kinds of amino acid residues necessary for self-alignment, which is a first step in fiber formation. For convenience, each such polypeptide is referred to as a minimal functional unit, or MFU. The secondary structure of an MFU according to the present invention comprises at least three consecutive beta-sheet/beta-turn structures. In some embodiments, the primary structure includes, in addition to and distinct from the residues forming the beta-sheet/beta-turn structures, at least one amino acid residue that is capable of participating in crosslinking. In some embodiments, the MFUs include those described in U.S. Pat. Nos. 5,969,106; 6,489,446 and 6,765,086, the entire contents of which are incorporated herein by reference.

As discussed above, beta-sheet and beta-turn structures are well known in the art. Beta-sheet structures of the polypeptides described herein are typically comprised of several amino acid residues, for example, from 3 to about 7 amino acid residues, including from about 5 to about 7 amino acid residues, such as from 5 to 7 amino acid residues. The amino acid residues of the beta-sheet structures may have hydrophobic side chains. Beta-turn structures in accordance with the present invention are typically initiated by two amino acid residues, often GG or PG, and may comprise additional amino acid residues. For example, a beta-turn structure in accordance with the present invention may comprise from about 2 to about 4 amino acid residues, including from 2 to 4 amino acid residues, and, in particular, 4 amino acid residues.

FIG. 1D is a schematic diagram of a peptide with consecutive beta-sheet/beta-turn structures. The shaded ribbon represents a peptide. The six straight portions of the ribbon represent the beta-sheet structures and the five curved portions of the ribbon represent the beta-turn structures. The empty circles represent hydrophobic side chains which are directed below the beta-sheets, and the shaded circles represent hydrophobic side chains which are directed above the beta-sheets. These hydrophobic side chains are on amino acid residues such as alanine, valine, isoleucine, leucine, tyrosine and phenylalanine. The rectangles indicate hydrogen bonds which stabilize the beta-turn structures. See also Robson et al., supra; Lehninger, supra, at pages 133-35.

The MFUs described herein are soluble, and exhibit the property of coacervation, aligning themselves in the same manner as the parent protein. For example, the hydrophobic sequences of the MFUs align in the same manner as the hydrophobic sequences of the parent proteins. When considering the secondary structure of the MFUs, this means that the beta-sheets of the MFUs are aligned with each other. This alignment occurs in the same manner as in the parent proteins, with the beta-sheets being stacked in a "lego"-type motif. See Robson, et al., supra. In elastin-derived MFUs (and with other MFUs comprising crosslinking residues), the alignment also results in the lysine residues (or other crosslinking residues) aligning in a manner that permits crosslinking between the MFUs.

In one embodiment, the synthetic polypeptide material comprises a polypeptide having the primary structure (that is, the amino acid sequence) of a portion of a naturally occurring fibrous protein (but not including the full-length sequence of the fibrous protein) and a secondary structure comprising at least three consecutive beta-sheet/beta-turn structures. In some embodiments, each of the beta-sheet/beta-turn structures comprises from 3 to about 7 amino acid residues. In further embodiments, the polypeptide also includes at least one crosslinking amino acid residue that participates in crosslinking, wherein the crosslinking residue is distinct from the beta-sheet/beta-turn structures.

Suitable polypeptides may be of varying weights and amino acid lengths. For example, in some embodiments the polypeptides weigh about 12 kD to about 45 kD, about 20 kD to about 40 kD, about 25 kD to about 35 kD, or about 30 kD to about 35 kD, such as from 12-45 kD, from 20-40 kD, from 25-35 kD, or from 30-35 kd. In some embodiments, the polypeptides comprise about 150 to about 500 amino acids, about 190 to about 450 amino acids, about 250 to about –400 amino acids, or about 325 to about 375 amino acids, such as from 150-500 amino acids, from 190-450 amino acids, from 250-400 amino acids, or from 325-375 amino acids.

While the description below uses MFUs modeled on elastin as exemplary MFUs, polypeptides modeled on other proteins are encompassed by the present invention. For example, polypeptides modeled on any other fiber-forming proteins, including spider silk, lamprin and resilin, are contemplated for use. These MFUs can be obtained as described herein for MFUs modeled on elastin. Moreover, mixtures of MFUs from two or more different parent proteins (e.g., MFUs modeled on lamprin, elastin, and resilin) can be used together to produce a variety of materials.

The domain structure of human elastin is illustrated in FIG. 1A. As shown in this Figure, there are a number of alternating crosslinking and hydrophobic domains. The hydrophobic domains each are believed to comprise a number of beta-sheet/beta-turn-forming sequences. These domains represent probable MFUs of elastin. One of these, used in further experimentation, is designated by the bracket and is named MFU-1. FIG. 1B sets forth the amino acid (SEQ ID NO:1) of human elastin. The underlined amino acid residues, residues 374-499, comprise MFU-1. Other MFUs modeled on human elastin include polypeptides comprising amino acid residues 19-160, 188-367 and 607-717, respectively. The amino acid sequence of MFU-3 (SEQ ID NO: 8; FIG. 4A) corresponds to that of MFU-1 without the first five amino acid residues. The amino acid sequence of MFU-4 (SEQ ID NO: 9; FIG. 4B) corresponds to that of MFU-1 without the first four amino acid residues. The amino acid sequence MFU-5 (SEQ ID NO: 10, FIG. 4C) corresponds to that of MFU-2 without the first amino acid.

MFUs modeled on human elastin comprise a portion of the amino acid sequence of the tropoelastin molecule (FIG. 1B; SEQ ID NO:1) and have at least three consecutive beta-sheet/beta-turn structures in their secondary structure. They also may comprise amino acids residues which are capable of participating in crosslinking, such as lysine residues. As noted above, in some embodiments the crosslinking residues are distinct from the residues forming the beta-sheet/beta-turn structures. In one embodiment, the MFU comprises two consecutive amino acid residues capable of participating in crosslinking in such a manner as to form a desmosine-type linkage. For example, the MFU may comprise a KAAK (SEQ ID NO:3) or KAAAK (SEQ ID NO:4) amino acid sequence. An MFU may include more than one occurrence of crosslinking residue(s), each of which may be distinct from residues forming beta-sheet/beta-turn structures.

In one embodiment, a polypeptide modeled on human elastin consists essentially of a portion of the amino acid sequence set forth in FIG. 1B (SEQ ID NO:1). The phrase "A consists essentially of B" herein denotes that A comprises B and possibly other components that do not materially affect the characteristics of the A-B material. For example, a polypeptide consisting essentially of a portion of the amino acid sequence set forth in FIG. 1B (SEQ ID NO:1) denotes a polypeptide which comprises a portion of the amino acid sequence set forth in FIG. 1B (SEQ ID NO:1) and which also may comprise other amino acid residues that do not materially alter the characteristics of the polypeptide. That is, the polypeptide maintains the characteristics of having at least three consecutive beta-sheet/beta-turn structures, and self-aligning in the same manner as tropoelastin peptides. It should be understood, however, that a polypeptide modeled on a parent protein that consists essentially of a portion of the amino acid sequence of the parent protein does not include the full-length amino acid sequence of the parent protein.

As described above, the secondary (beta-sheet/beta-turn) structure of the MFUs is believed to guide the self-aggregation and self-alignment of the MFUs such that the MFUs align themselves in a manner that mimics the structure of aggregates of the parent protein. For example, the beta-sheets of the MFUs are aligned, and the lysine residues of elastin-modeled MFUs (and other MFUs comprising crosslinking residues) are aligned for enzymatic or chemical crosslinking into stable polymeric structures, mimicking the way tropoelastin monomers form the elastin protein.

An MFU can be obtained by any method, including direct synthesis or recombinant production of the peptide. For example, the DNA for an MFU modeled on human elastin can be obtained directly from DNA coding for human elastin either by cleavage of the DNA and selection of the appropriate segment, or by synthesis of the DNA via a variety of well-known methods.

By means of available technology, DNA sequences coding for tandem repeats of any human elastin MFU, or for MFUs containing larger domains of human elastin, up to and including the entire tropoelastin molecule, can be constructed, although in some embodiments the polypeptide does not include the full length sequence of elastin. These larger elastin sequences may offer advantages in terms of their kinetics of assembly or their mechanical properties. For example, MFU-2, which consists of exons 20, 21, 23, 24, 21, 23, and 24 of human elastin, has been expressed and purified. The amino acid sequence of this peptide is set forth in FIG. 3C (SEQ ID NO:2). MFU-2 demonstrates an increased tendency towards spontaneous self-aggregation than MFU-1, as evidenced by a lower coacervation temperature. The amino acid sequence of MFU-5 (FIG. 4C; SEQ ID NO: 10) corresponds to that of MFU-2 without the first amino acid residue.

In addition, MFU-6 and MFU-7 correspond to the molecules MFU-2 and MFU-5 with two additional segments of the crosslinking and exon 24 portions of the molecule. See FIGS. 3C, 4C, 5A, and 5B. MFU-2, MFU-5, MFU-6, and MFU-7 are exemplary embodiments of polypeptides useful in materials for joint cushioning applications.

Also useful in the synthetic polypeptide materials described herein is a polypeptide comprising the primary structure of a portion of a naturally occurring fibrous protein (but not including the full-length sequence of the fibrous protein) wherein the primary structure is modified by the addition, substitution and/or deletion of one or more amino acid residues. The polypeptide has a secondary structure comprising at least three consecutive beta-sheet/beta-turn structures and exhibits the properties of self-alignment described herein. While there is no set limit on the number of modifications that could be made, it is believed that modifications involving the addition, substitution and/or deletion of from 1 to about 20, from 1 to about 10, from 1 to about 5, amino acid residues, relative to the corresponding sequence of the parent protein, can be effected while maintaining the above-described properties of the polypeptide. Thus, polypeptides comprising from 1-20, 1-10 or 1-5 amino acid additions, substitutions and/or deletions, relative to the corresponding sequence of the parent protein, are suitable.

In some embodiments, only conservative amino acid alterations are undertaken. Illustrative amino acid substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

For example, modifications in the hydrophobic regions of the polypeptide may comprise substituting one or more of the amino acids residues at the beta-turns with other amino acids that initiate beta-turns. For example, one or more of the P or G residues may be replaced with a G or P residue, respectively, or may be replaced with a serine residue. Additionally or alternatively, modifications may be made to the amino acid residues in the beta-sheet structure, such as the addition, deletion or substitution of one or more amino acid residues. For example, an amino acid residue having a hydrophobic side chain can be replaced by a different amino acid residue having a hydrophobic side chain, or having a side chain with similar properties. Exemplary substitutions include intersubstitutions of alanine, valine, isoleucine, leucine, tyrosine and phenylalanine.

For polypeptides comprising a crosslinking domain (e.g., comprising at least one crosslinking amino acid residue), any number of additions, substitutions and deletions can be made that do not interfere with the alpha-helical structure of the crosslinking domain, such as additions, deletions, and conservative amino acid substitutions, as discussed above. Also, lysine residues can be replaced with any other amino acid residue that could participate in crosslinking, such as tyrosine or acidic or basic residues, including arginine, aspartic acid and glutamic acid.

In accordance with one embodiment, a polypeptide is used whose amino acid sequence comprises a variant of a portion (or fragment) of the amino acid sequence set forth in FIG. 1B (SEQ ID NO:1). The amino acid sequence of such a polypeptide corresponds to a portion of the amino acid sequence set forth in FIG. 1B (SEQ ID NO:1), wherein the amino acid sequence set forth in the Figure is modified by the addition, deletion, or substitution of from 1 to about 10 amino acid residues, for example, from 1 to about 5 amino acid residues, including from 1 to 10 or 1 to 5 amino acid additions, deletions, or substitutions. Such a polypeptide has a secondary structure comprising at least three consecutive beta-sheet/beta-turn structures and exhibits the properties of self-alignment described herein.

Figure 3A:
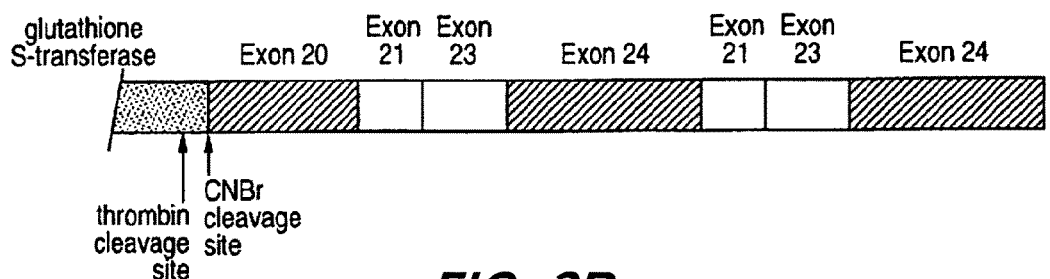
FIG. 3A shows a GST fusion construct capable of expressing the polypeptide MFU-2.
Figure 3B:
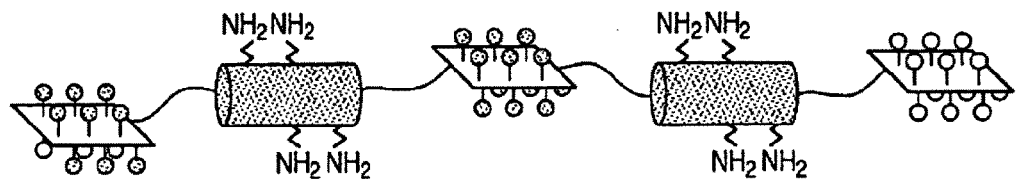
FIG. 3B is a cartoon representation of the hydrophobic and crosslinking domains of MFU-2.

In accordance with another embodiment, a polypeptide is used whose amino acid sequence comprises a variant of the amino acid sequence set forth in FIG. 3C, known as MFU-2 (SEQ ID NO:2). The amino acid sequence of such a polypeptide corresponds to a portion of the amino acid sequence set forth in FIG. 3C (SEQ ID NO:2), wherein the amino acid sequence set forth in the Figure is modified by the addition, deletion, or substitution of from 1 to about 10 amino acid residues, for example, from 1 to about 5 amino acid residues, including from 1 to 10 or 1 to 5 amino acid additions, deletions, or substitutions. Such a polypeptide has a secondary structure comprising at least three consecutive beta-sheet/beta-turn structures and exhibits the properties of self-alignment described herein.

Polypeptides whose amino acid sequences comprise variants of the amino acid sequences set forth in FIGS. 4A-4C (SEQ ID NOS: 8-10, respectively) also are encompassed by the present invention. The amino acid sequences of such polypeptides comprise a portion of an amino acid sequence set forth in FIG. 4A, 4B or 4C (SEQ ID NOS: 8, 9 or 10, respectively), wherein the amino acid sequence set forth in the Figure is modified by the addition, deletion or substitution of from 1 to about 10 amino acid residues, for example, from 1 to about 5 amino acid residues, including from 1 to 10 or 1 to 5 amino acid additions, deletions, or substitutions. Such polypeptides have a secondary structure comprising at least three consecutive beta-sheet/beta-turn structures and exhibit the properties of self-alignment discussed herein.

Polypeptides whose amino acid sequences comprise variants of the amino acid sequences set forth in FIGS. 5A-5B (SEQ ID NOS: 12-13, respectively) also are encompassed. The amino acid sequences of such polypeptides comprise a portion of an amino acid sequence set forth in FIGS. 5A-5B (SEQ ID NOS:12 or 13, respectively), wherein the amino acid sequence set forth in the Figure is modified by the addition, deletion or substitution of from 1 to about 10 amino acid residues, for example, from 1 to about 5 amino acid residues, including from 1 to 10 or 1 to 5 amino acid additions, deletions, or substitutions. Such polypeptides have a secondary structure comprising at least three consecutive beta-sheet/beta-turn structures and exhibit the properties of self-alignment discussed herein.

An MFU modeled on human elastin in accordance with the present invention offers distinct advantages over other elastin preparations. For example, in contrast to the solubilized fragments of elastin used before, an MFU is a single peptide of defined composition. The MFU is considerably smaller than the parent protein and simpler in structure, and therefore is easier to produce or express in quantity, to handle in solution, and to manipulate for experimental and practical purposes. Like other elastin preparations, the MFU is non-thrombogenic and provides a friendly environment for cell infiltration. In addition, being composed entirely of a human elastin sequence, an MFU is non-immunogenic, thus providing a truly biocompatible material.

Joint Reconstruction, Repair and Cushioning

As set forth above, the polypeptides (e.g., MFUs) described herein are suitable for use in materials for joint reconstruction, repair and cushioning applications. The polypeptides can be fabricated into synthetic polypeptide materials that are useful as joint cushions, for example, to provide a cartilage-like structure between bones or in joints. Additionally or alternatively, materials fabricated from the polypeptides can be used as plug material to repair localized damages to articular joint surfaces. Suitable materials can be obtained from the polypeptides by a process including coacervation and crosslinking, as described below. Additionally, suitable materials can be formed in situ, such as by injecting a solution or suspension of synthetic polypeptides into a joint site under conditions such that coacervation and assembly occurs in situ as the synthetic polypeptides are exposed to in vivo conditions.

A characteristic property of the polypeptides described herein is their ability to self-assemble in an ordered manner, in the same manner as the tropoelastin monomers of human elastin. For example, the polypeptides align themselves in an order that aligns their beta-sheet structures and that permits crosslinking between the individual peptides, when the polypeptide is modeled on elastin or otherwise includes amino acid residues capable of participating in crosslinking. This process of self-alignment and self-aggregation is considered to be the first step in fiber formation. The fibers then can be made into a material that has chemical and structural properties similar to those of natural elastin polymers.

Thus, while the polypeptides described herein are normally soluble in solution, simple manipulations of pH, salt content and temperature initiate coacervation and self-alignment of the polypeptides, resulting in aggregates of elastin-like fibers. The exact conditions that will bring about coacervation and self-alignment of the polypeptides varies depending on the polypeptide and the solution to be manipulated. Conditions that bring about coacervation are well-known to those skilled in the art, and those skilled in the art can induce coacervation and self-alignment of polypeptides by following routine laboratory procedures.

Figure 2:
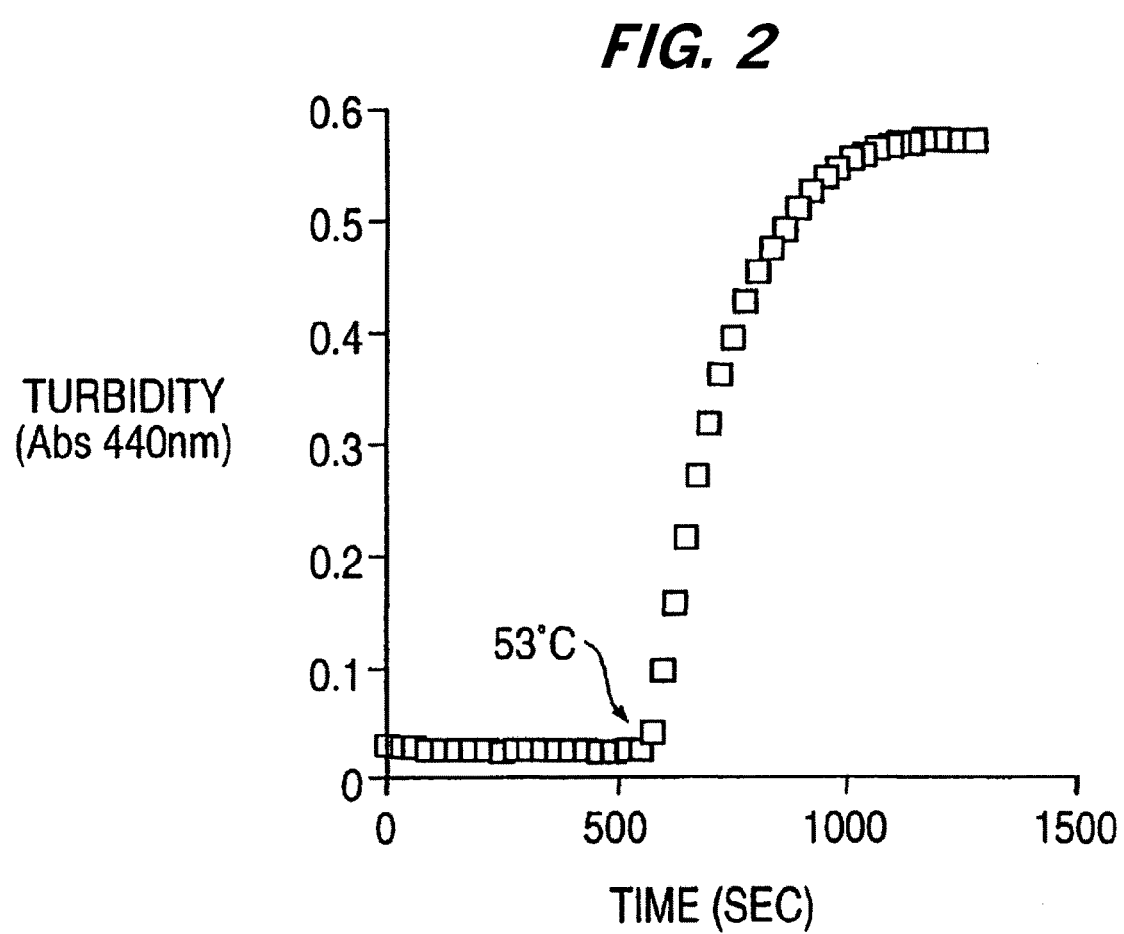
FIG. 2 illustrates the coacervation (self-aggregation) of MFU-1.

FIG. 2 illustrates the ability of the polypeptides described herein to coacervate. In particular, FIG. 2 illustrates the coacervation (self-aggregation) of MFU-1 of human elastin. The peptide was dissolved at a concentration of 0.25 mg/ml in phosphate-buffered saline, pH 7.4, containing 1.5 M NaCl and 0.3 mM $CaCl_2$, and the temperature of the solution was raised at a uniform rate. The onset of coacervation occurred at 53° C., and is indicated by an increase in turbidity of the solution.

As noted above, the synthetic polypeptide materials described herein may be made from a single type of polypeptide (e.g., polypeptides having the same amino acid sequence), or may comprise different polypeptides modeled on the same or different parent proteins. For example, the material may be comprised of any single polypeptide modeled on human elastin (e.g., any one of MFUs 1-7), a combination of two or more polypeptides modeled on human elastin (e.g., two or more of any of MFUs 1-7), or a combination of one or more polypeptides modeled on one or more different parent proteins (e.g., including one or more polypeptides modeled on human elastin and one or more polypeptides modeled on fibrin or resilin). In one embodiment, the material is composed of one or more polypeptides selected from MFU-2, MFU-5, MFU-6 and MFU-7.

Materials comprised of combinations of different polypeptides modeled on the same or different parent proteins can be chosen to form a material with desired physical properties. For example, a combination of a polypeptide modeled on elastin and a polypeptide modeled on spider silk protein will have the high extensibility of elastin and the high tensile strength of spider silk protein. Appropriate selection of the polypeptides and their relative amounts permits the production of materials with specified properties.

Combination materials may be obtained by different methods, such as by coacervating solutions comprising the different polypeptides, using fusion proteins comprising the amino acid sequences of two or more polypeptides, or using two or more polypeptides chemically linked together. For example, in one embodiment, a polypeptide is used that comprises an MFU modeled on elastin, such as animal or human elastin, and an MFU modeled on another fibrous protein, such as lamprin or a spider silk protein. Such a polypeptide can be made by methods known to those skilled in the art, for example, by methods used to make fusion proteins. A polypeptide comprising exons 21 and 22 of human elastin flanked on both sides by tandem repeat sequences from lamprin has been expressed as a fusion protein. In an alternative embodiment, a material is provided which comprises an MFU modeled on animal or human elastin chemically-linked to an MFU modeled on lamprin or a spider silk protein. Such chemically-linked polypeptides can be made by methods known to those skilled in the art. Other combinations of MFUs modeled on the same or different parent proteins also are useful in the materials described herein.

In one embodiment, a polypeptide is designed that comprises a crosslinking domain of resilin with an MFU modeled on a fibrous protein, such as human elastin (as described above). Resilin is a protein polymer which is present in the wing hinges of insects and provides the functional properties of a compressive elastomer. The polymeric form of resilin is naturally crosslinked by dityrosine and trityrosine bridges between the protein chains. The sequence of monomeric resilin has been published, and the monomeric proteins have been crosslinked in vitro under oxidative conditions, resulting in the formation of the native crosslinks, dityrosine, and trityrosine. See, e.g., Elvin et al., Nature 437: 999-1002 (2005). Once aligned, the resilin crosslinking domains can be crosslinked into polymers using, for example, hydrogen peroxide and peroxidase. Materials comprising polypeptides with these resilin-based crosslinks may have superior properties and compressive elasticity and resilience and compressibility that make them particularly suitable for use in joint cushioning applications, where these properties are desirable.

In some embodiments, the synthetic polypeptide material comprises a polypeptide modeled on lamprin. Such a polypeptide comprises a portion of the amino acid sequence of lamprin that has at least three consecutive beta-sheet/beta-turn structures, but does not include the full-length lamprin amino acid sequence. In one embodiment, a polypeptide modeled on lamprin consists essentially of a portion of the amino acid sequence of lamprin, as the phrase "consists essentially of" is defined above. Alternatively, a polypeptide modeled on lamprin comprises a portion of the amino acid sequence of lamprin, wherein the amino acid sequence is modified by one or more additions, substitutions and/or deletions, as described above, including 1-10 or 1-5 amino acid modifications.

In addition, the synthetic polypeptide material may comprise other proteins in addition to the polypeptides modeled on a fibrous protein. For example, polypeptides modeled on a fibrous protein can be co-aggregated with other proteins, for example collagen, to provide cushion material that resembles the natural structural materials of the body.

The synthetic polypeptide materials also may include non-protein materials, including hydrophilic polymers, such as glycosaminoglycans, e.g., hyaluronan. Such materials may comprise mixtures of the components, or may involve crosslinking between the components. For example, the materials may comprise glycosaminoglycan moieties linked covalently to polypeptides through functional groups on the polypeptides, where the functional groups are normally present on the polypeptide, or are introduced into the polypeptide by methods known in the art.

The synthetic polypeptide materials described herein are biocompatible, and are subject to infiltration of cells growing in the patient, including endothelial cells. As a result, implanted material can become a permanent, living, tissue replacement.

Thus, described herein are synthetic polypeptide materials for joint reconstruction, repair and cushioning comprising polypeptides modeled on fibrous proteins, e.g., comprising MFUs. As set forth above, these materials are obtained by coacervating the polypeptides, crosslinking the polypeptides, and, optionally, fabricating the material into sheets or pads or providing them as liquid suspensions or solutions in pharmaceutically acceptable carriers for injection. As discussed above, in accordance with some embodiments, the polypeptides and/or crosslinking agents are selected to provide a synthetic polypeptide material that has an increased compressibility as compared to a comparable material made from elastin.

In some embodiments, the synthetic polypeptide materials consist essentially of the crosslinked polypeptides. By a polypeptide material that "consists essentially of the crosslinked polypeptides" is meant a material that does not include other material providing structural support, such as a core or reinforcing structure of animal material, synthetic material or metal. In some embodiments, the material consists of the crosslinked polypeptides.

In some embodiments, the synthetic polypeptide materials consist essentially of the crosslinked polypeptides and non-protein material (e.g., hydrophilic polymer, such as glycosaminoglycan, for example, hyaluronan). For example, a polypeptide material that "consists essentially of the crosslinked polypeptides and glycosaminoglycan moieties" refers to a material that does not include other material providing structural support, such as a core or reinforcing structure of animal material, synthetic material or metal. In some embodiments, the material consists of the crosslinked polypeptides and glycosaminoglycan moieties.

Also described herein are synthetic polypeptide materials comprising a reinforcing material such as a core that is coated with the polypeptide materials described herein, or a reinforcing structure that is embedded in, or sandwiched between layers of, the synthetic polypeptide material. In some embodiments, the core or reinforcing structure is an animal material, synthetic material, or metal. Such coated or reinforced materials offer many of the same advantages as materials that lack such structures, including being biocompatible, non-immunogenic, and providing an environment for cell infiltration. The addition of core or reinforcing materials to the synthetic polypeptide materials may enhance certain properties. For example, a particular application may require a density or rigidity which cannot be attained using solely a crosslinking agent and polypeptides. Inclusion of reinforcing animal material, synthetic material, or metal allows for the preparation of materials with specific physical characteristics.

In accordance with some embodiments, there is provided methods for the reconstruction, repair or cushioning of a joint that comprises inserting (including placing or injecting) the synthetic polypeptide material described herein into the joint or into a site near the joint, such as a tissue area, such as the intervertebral disk space.

In some embodiments, the synthetic polypeptide materials (or sheets or pads formed therefrom) are inserted in joint locations in order to cushion bone-bone contacts, such as via surgical methods. As noted above, exemplary joints include, but are not restricted to, hips knees, elbows, shoulders and digits, as well as at intervertebral sites. In some embodiments, the synthetic polypeptide materials (or sheets or pads formed therefrom) are placed in situ and are anchored by sutures, adhesives, by press-fitting into depressions surgically created in bone surfaces, or by any other suitable means. In other embodiments, the synthetic polypeptide materials (or sheets or pads formed therefrom) are placed in situ and are not anchored by any other means. In some embodiments, the materials are provided as ligament-like structure that may be surgically inserted to reconstruct, repair and/or stabilize joints. While not wanting to be bound by any theory, it is believed that, in some embodiments, synthetic polypeptide materials may be anchored in place over time, as tissue grows into the material.

In some embodiments, the synthetic polypeptide materials are provided in liquid soluble or suspended forms, in pharmaceutically acceptable carriers for injection, and are injected into joint locations or tissue spaces, for example, to provide a cushion between bony surfaces. As discussed above, in accordance with these embodiments, the synthetic polypeptides may coacervate and undergo self-assembly upon exposure to in vivo conditions, such as body temperature, thereby forming solid synthetic polypeptide materials in situ.

The present invention is further illustrated below by reference to the following examples. The examples are illustrative only, and are not to be construed as limiting the scope of the invention.

EXAMPLES

Example 1

A pad of synthetic peptide material was fabricated by coacervation of a polypeptide modeled on elastin (MFU-7) from solution at 37° C., followed by centrifugation. In particular, the polypeptide was dissolved to a concentration of 50 mg/ml in 0.15M borate buffer, pH 8.0, in a flat-bottomed container. The solution was adjusted to 0.8 M in NaCl to initiate coacervation. The coacervate was centrifuged at 12,000×g for 15 min at 37° C. Then 500 µl of 10 µM genipin was added and centrifugation at 12,000×g at 37° C. is continued for an additional 30 minutes to form a pad. The material was allowed to mature overnight at 37° C., and then stored in water until use.

Figure 6:
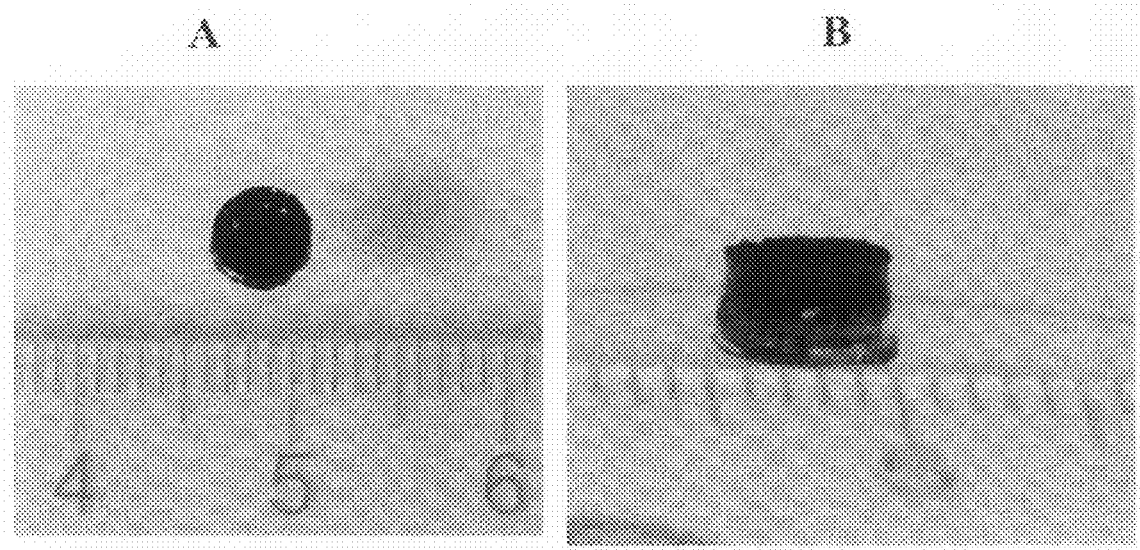
FIG. 6 shows a typical pad of elastin-like material.

FIG. 6 shows a typical pad prepared in this manner, approximately 3 mm in diameter and 3 mm in thickness.

Figure 7:
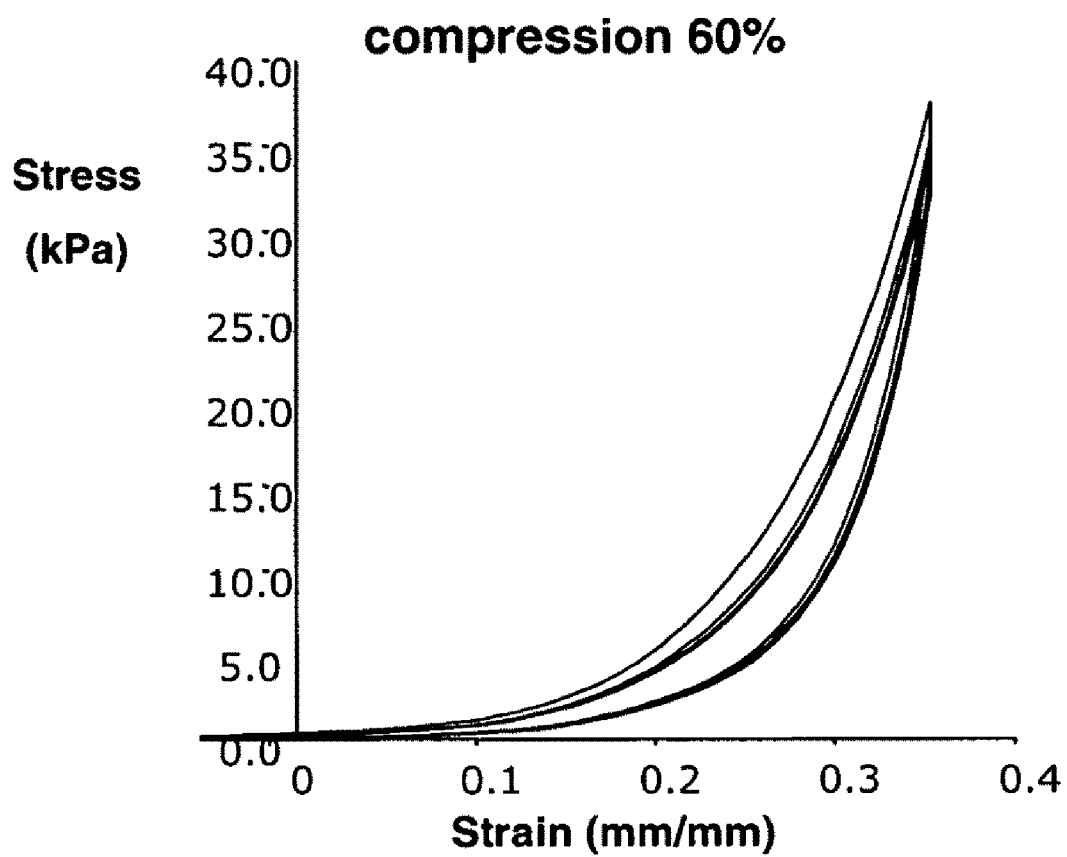
FIG. 7 shows results of compression testing of the pad shown in FIG. 6, demonstrating the resistance to compression and the resilience and compressibility of the material.
Figure 8:
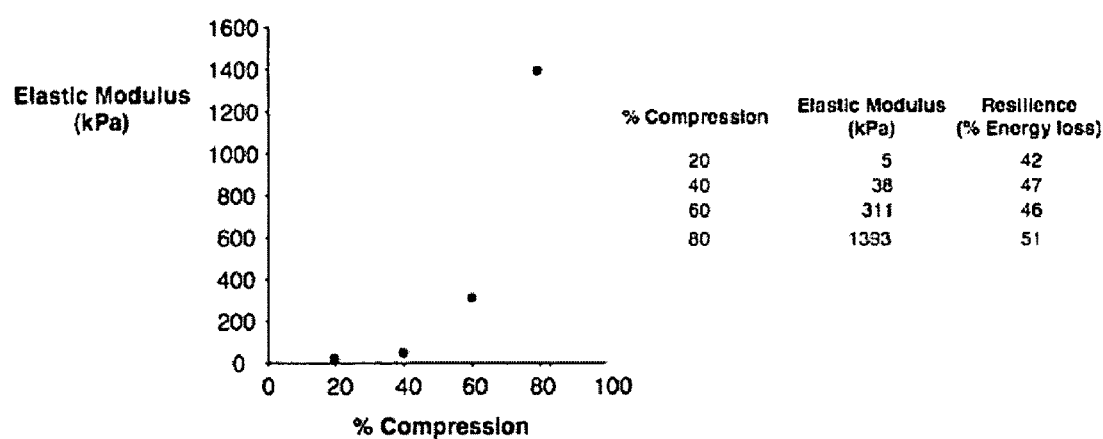
FIG. 8 gives typical elastic modulus and resilience (energy loss) and compressibility characteristics of the material in FIG. 6, at different degrees of compression.

To assess resistance to compression and resilience (e.g., compressibility), the pad was subject to compression testing by routine methods using a Biosyntech Mach-1 testing apparatus (Biosyntech Inc., Laval, QC). The elastic modulus and resilience (energy loss) and compressibility characteristics of the material were measured at different degrees of compression by routine methods using a Biosyntech Mach-1 testing apparatus (Biosyntech Inc., Laval, QC). Results are set forth in FIGS. 7 and 8 and in the table below:

| % Compression | Elastic Modulus (kPa) | Resilience (% Energy Loss) |
| --- | --- | --- |
| 20 | 5 | 42 |
| 40 | 38 | 47 |
| 60 | 311 | 46 |
| 80 | 1393 | 51 |

These results demonstrate that the material has a significant resistance to compression (elastic modulus) and that the material returns with good resilience to its pre-compression dimensions (e.g., compressibility), even after several cycles of loading and unloading.

Example 2

Figure 9:
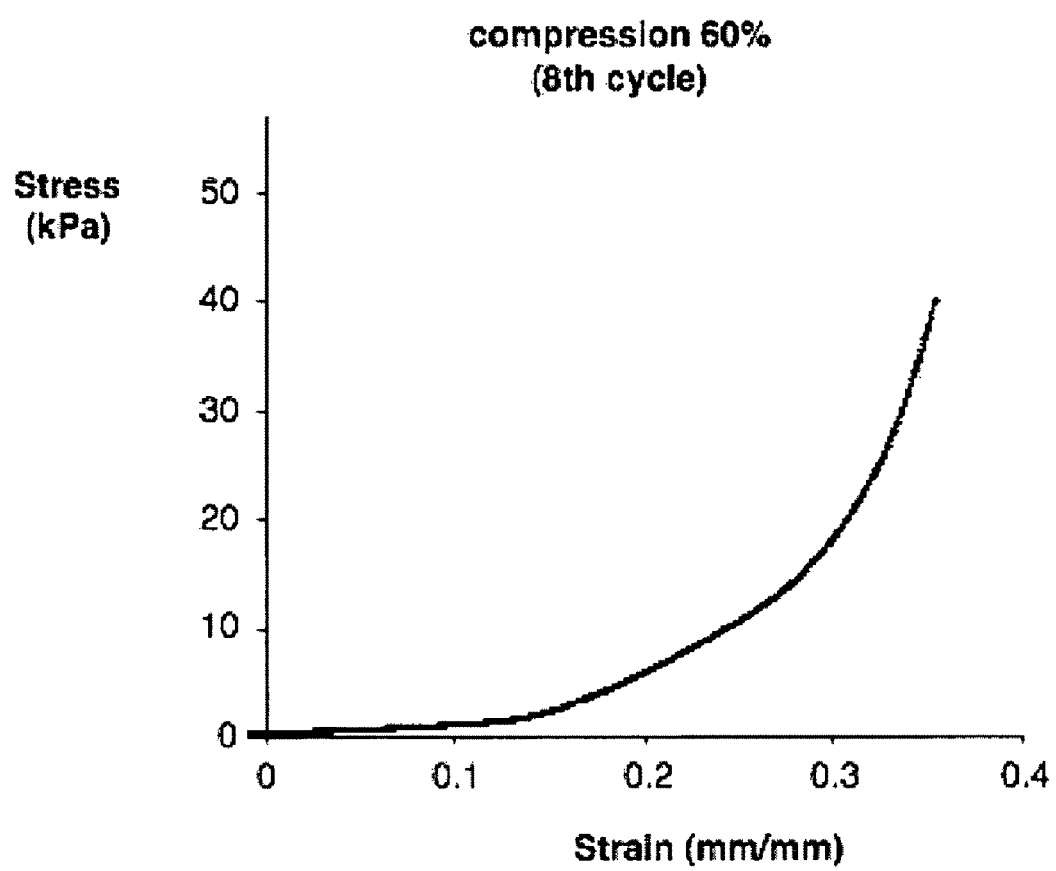
FIG. 9 shows the results of compression testing and resilience and compressibility of a pad of elastin-like material prepared by the foaming technique outlined in Example 2.
Figure 10:
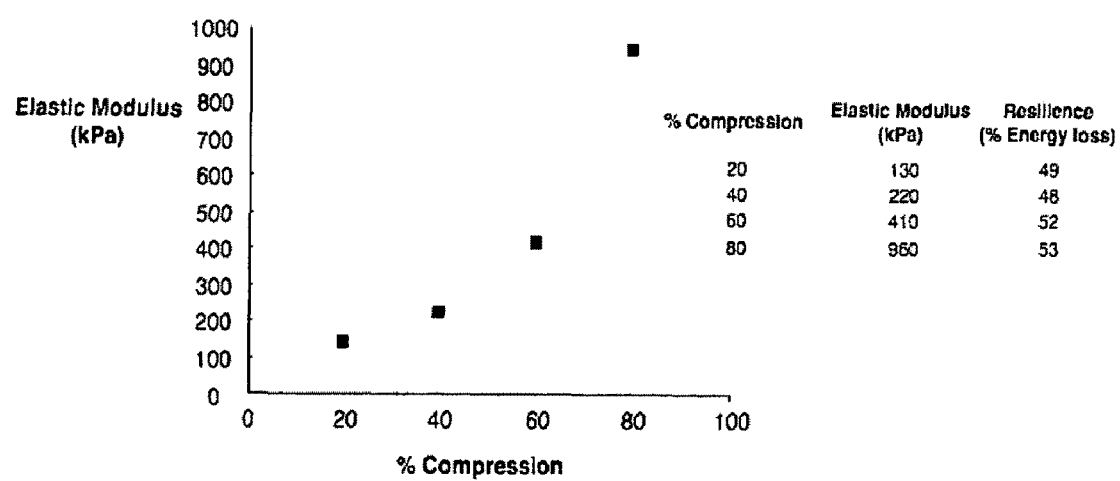
FIG. 10 gives typical elastic modulus and resilience (energy loss) and compressibility characteristics of the material prepared in Example 2 at different degrees of compression.

A pad of synthetic peptide material was fabricated from a solution of a polypeptide modeled on elastin (MFU-7) using a foaming technique involving crosslinking with lysine-diisocyanate. In particular, the polypeptide was dissolved to 10 mg/ml in DMSO and warmed to 65° C. under nitrogen for 20 minutes. 697 µL of water was added, followed by drop wise addition of 303 µL of lysine-diisocyanate. The sample was mixed and left in room air at 20° C. overnight. The insoluble, crosslinked material was then lyophilized and stored in water until use. In this example, the dimensions of the pad of material is dictated by the container in which the material is made. The physical properties of the material were assessed as described above in Example 1. Results are set forth in FIGS. 9 (compression testing and resilience) and 10 (elastic modulus and resilience at difference degrees of compression) and in the table below:

| % Compression | Elastic Modulus (kPa) | Resilience (% Energy Loss) |
| --- | --- | --- |
| 20 | 130 | 49 |
| 40 | 220 | 48 |
| 60 | 410 | 52 |
| 80 | 960 | 53 |

Again, the results show that the material has a significant resistance to compression (elastic modulus) and returns with good resilience to its pre-compression dimensions even after several cycles of loading and unloading.

Example 3

Sheets of synthetic peptide material were fabricated by coacervation of a polypeptide modeled on elastin (MFU-7) from solution at 37° C., followed by centrifugation, following the same general procedures as outlined above, but using different crosslinking agents. As shown in the table below, the specific crosslinking agent used impacted the elastic modulus of the material.

| Crosslinker | Elastic Modulus (kPa) |
|---|---|
| Genipin | 1434 |
| Glyoxal | 1065 |
| Methyglyoxal | 638 |
| PQQ | 337 |

Thus, the selection of a specific crosslinking agent can be used to design materials with target elastic modulus properties.

Example 4

Sheets of synthetic peptide material were fabricated from different polypeptides modeled on elastin according to the general procedures described above, e.g., coacervation from solution at 37° C., followed by centrifugation and crosslinking with pyrroloquinoline quinone. As shown in the table below, the elastic modulus of the material varied with the polypeptide.

| Polypeptide | Elastic Modulus (kPa) |
|---|---|
| MFU-5 | 190 |
| MFU-7 | 350 |

These results demonstrate that a polypeptide with a larger number of repeating units (MFUs) results in a material with an increased elastic modulus. Thus, the selection of polypeptides comprising a greater or fewer numbers of such units permits the design of materials with target elastic modulus properties.

Example 5

Pads of synthetic polypeptide material fabricated by coacervation of a polypeptide modeled on elastin as described in Example 1 and with properties described in Example 2 were press-fit into drill hole defects created in the articular joint surface of the knees of rabbits. The knees were then closed and the rabbits allowed to recover and resume normal ambulation. Six weeks after the operation, the rabbits were ambulating normally with no evidence of pain, and the pads were found to be firmly in place with no evidence of rejection of the pad, or inflammation in the surrounding tissues or synovial fluid. Qualitative analysis of synovial fluid in the knee joints six weeks after placement of the pad of material as compared to control rabbits with unfilled drill hole defects showed no evidence of inflammation in the treated rabbits:

|  | 6 Week Treated | 6 Week Control |
|---|---|---|
| Average volume (mL, ±SD) | 75 ± 50 | 45 ± 40 |
| Clarity | Transparent (4/4) | Transparent (4/4) |
| Viscosity | High | High |

Moreover, magnetic resonance imaging at 6 weeks after implantation showed evidence of incorporation of regenerated host tissue into the periphery of the pad, indicating excellent biocompatibility of the implanted material.

It will be apparent to those skilled in the art that various modifications and variations can be made to the processes and compositions described herein. Thus, it is intended that the present invention includes any such modifications and variations.

What is claimed is:

1. A method for the reconstruction, repair or cushioning of a joint comprising inserting into the joint, or into a site near the joint, a synthetic polypeptide material comprising crosslinked polypeptides, wherein each polypeptide is between 150 and 500 amino acids in length and comprises
    (A) at least three consecutive beta-sheet/beta-turn structures consisting of a portion of the amino acid sequence of a protein selected from the group consisting of elastin, lamprin, spider silk protein, and resilin, wherein the amino acid sequence of said three consecutive beta-sheet/beta-turn structures may be modified by the addition, deletion or substitution of from 1 to about 10 amino acid residues relative to the portion of the amino acid sequence of said protein, and
    (B) at least one crosslinking amino acid residue distinct from and alternating with the at least three consecutive beta-sheet/beta turn structures that participates in crosslinking.

2. The method of claim 1, wherein each of the beta-sheet structures of the crosslinked polypeptides comprises from 3 to about 7 amino acid residues.

3. The method of claim 1, wherein at least one polypeptide of the synthetic polypeptide material comprises an amino acid sequence that consists of a portion of the amino acid sequence of a protein selected from the group consisting of: elastin, lamprin, spider silk protein, and resilin.

4. The method of claim 1, wherein at least one polypeptide of the synthetic polypeptide material comprises an amino acid sequence consisting of a portion of the amino acid sequence of human elastin, optionally modified by the addition, deletion or substitution of from 1 to about 10 amino acid residues relative to the portion of the amino acid sequence of elastin.

5. The method of claim 1, wherein at least one polypeptide of the synthetic polypeptide material comprises an amino acid sequence consisting of a portion of the amino acid sequence set forth in FIG. 1B (SEQ ID NO:1).

6. The method of claim 5, wherein the polypeptide comprises an amino acid sequence selected from the group consisting of amino acid residues 374-499, 19-160, 188-367 and 607-717 of FIG. 1B (SEQ ID NO:1).

7. The method of claim 1, wherein at least one polypeptide of the synthetic polypeptide material comprises an amino acid sequence consisting of a portion of the amino acid sequence set forth in FIG. 1B (SEQ ID NO:1), modified by the addition, deletion or substitution of from 1 to about 10 amino acid residues.

8. The method of claim 1, wherein the polypeptide comprises tandem repeats of a portion of the amino acid sequence set forth in FIG. 1B (SEQ ID NO:1).

9. The method of claim 1, wherein the polypeptide comprises an amino acid sequence selected from the group consisting of the amino acid sequences set forth in FIG. 3C (SEQ ID NO:2), FIG. 4C (SEQ ID NO:10), FIG. 5A (SEQ ID NO:11), and FIG. 5B (SEQ ID NO:12).

10. The method of claim 1, wherein the polypeptide comprises an amino acid sequence selected from the group consisting of the amino acid sequences set forth in FIG. 3C (SEQ ID NO:2), FIG. 4C (SEQ ID NO:10), FIG. 5A (SEQ ID NO:11), and FIG. 5B (SEQ ID NO:12), modified by the addition, deletion or substitution of from 1 to about 10 amino acid residues.

11. The method of claim 1, wherein the amino acid sequences of said crosslinked polypeptides are the same.

12. The method of claim 1, wherein the amino acid sequences of said crosslinked polypeptides are different.

13. The method of claim 1, wherein at least one polypeptide of the synthetic polypeptide material comprises an amino acid sequence that consists of a portion of the amino acid sequence of resilin.

14. The method of claim 1, wherein the synthetic polypeptide material further comprises a reinforcing material.

15. The method of claim 14, wherein the reinforcing material is selected from the group consisting of an animal material, a synthetic material and metal.

16. The method of claim 1, wherein the synthetic polypeptide material further comprises a non-protein hydrophilic polymer.

17. The method of claim 1, wherein the synthetic polypeptide material further comprises glycosaminoglycan moieties.

18. The method of claim 17, wherein said glycosaminoglycan moieties comprise hyaluronan moieties.

19. The method of claim 17, wherein the synthetic polypeptide material comprises a mixture of said crosslinked polypeptides and said glycosaminoglycan moieties.

20. The method of claim 17, wherein said crosslinked polypeptides are covalently linked to said glycosaminoglycan moieties.

21. The method of claim 1, wherein the synthetic polypeptide material is a solid.

22. The method of claim 1, wherein the synthetic polypeptide material is in a form selected from the group consisting of pads, sheets and ligament-like structures.

23. The method of claim 1, wherein the synthetic polypeptide material is a liquid.

24. The method of claim 1, wherein the synthetic polypeptide material is in a solution or suspension that further comprises a pharmaceutically acceptable carrier suitable for injection.

* * * * *

SEQUENCE LISTING

<160> NUMBER OF SEQ ID NOS: 12

<210> SEQ ID NO 1
<211> LENGTH: 731
<212> TYPE: PRT
<213> ORGANISM: Homo sapiens

<400> SEQUENCE: 1

```
Gly Gly Val Pro Gly Ala Ile Pro Gly Gly Val Pro Gly Gly Val Phe
  1               5                  10                  15

Tyr Pro Gly Ala Gly Leu Gly Ala Leu Gly Gly Gly Ala Leu Gly Pro
             20                  25                  30

Gly Gly Lys Pro Leu Lys Pro Val Pro Gly Gly Leu Ala Gly Ala Gly
         35                  40                  45

Leu Gly Ala Gly Leu Gly Ala Phe Pro Ala Val Thr Phe Pro Gly Ala
     50                  55                  60

Leu Val Pro Gly Gly Val Ala Asp Ala Ala Ala Ala Tyr Lys Ala Ala
 65                  70                  75                  80

Lys Ala Gly Ala Gly Leu Gly Gly Val Pro Gly Val Gly Gly Leu Gly
                 85                  90                  95

Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
```

```
                  115                 120                 125
Leu Pro Gly Ala Arg Phe Pro Gly Val Gly Val Leu Pro Gly Val Pro
130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Tyr Gly
                180                 185                 190

Leu Pro Tyr Thr Thr Gly Lys Leu Pro Tyr Gly Tyr Gly Pro Gly Gly
                195                 200                 205

Val Ala Gly Ala Ala Gly Lys Ala Gly Tyr Pro Thr Gly Thr Gly Val
210                 215                 220

Gly Pro Gln Ala Ala Ala Ala Ala Ala Lys Ala Ala Lys Phe
225                 230                 235                 240

Gly Ala Gly Ala Ala Gly Val Leu Pro Gly Val Gly Ala Gly Val
                245                 250                 255

Pro Gly Val Pro Gly Ala Ile Pro Gly Ile Gly Gly Ile Ala Gly Val
                260                 265                 270

Gly Thr Pro Ala Ala Ala Ala Ala Ala Ala Ala Lys Ala Ala
                275                 280                 285

Lys Tyr Gly Ala Ala Ala Gly Leu Val Pro Gly Pro Gly Phe Gly
                290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu Ala Ala Ala Lys Ala Ala Ala
                340                 345                 350

Lys Ala Ala Lys Tyr Gly Ala Arg Pro Gly Val Gly Val Gly Gly Ile
                355                 360                 365

Pro Thr Tyr Gly Val Gly Ala Gly Gly Phe Pro Gly Phe Gly Val Gly
                370                 375                 380

Val Gly Gly Ile Pro Gly Val Ala Gly Val Pro Ser Val Gly Gly Val
385                 390                 395                 400

Pro Gly Val Gly Gly Val Pro Gly Val Gly Ile Ser Pro Phe Ala Gln
                405                 410                 415

Ala Ala Ala Ala Ala Lys Ala Ala Lys Tyr Gly Val Gly Thr Pro Ala
                420                 425                 430

Ala Ala Ala Ala Lys Ala Ala Lys Ala Ala Gln Phe Gly Leu Val
                435                 440                 445

Pro Gly Val Gly Val Ala Pro Gly Val Gly Val Ala Pro Gly Val Gly
                450                 455                 460

Val Ala Pro Gly Val Gly Leu Ala Pro Gly Val Gly Val Ala Pro Gly
465                 470                 475                 480

Val Gly Val Ala Pro Gly Val Gly Val Ala Pro Gly Ile Gly Pro Gly
                485                 490                 495

Gly Val Ala Ala Ala Ala Lys Ser Ala Ala Lys Val Ala Ala Lys Ala
                500                 505                 510

Gln Leu Arg Ala Ala Ala Gly Leu Gly Ala Gly Ile Pro Gly Leu Gly
                515                 520                 525

Val Gly Val Gly Val Pro Gly Leu Gly Val Gly Ala Gly Val Pro Gly
                530                 535                 540
```

```
Leu Gly Val Gly Ala Gly Val Pro Gly Phe Gly Ala Gly Ala Asp Glu
545                 550                 555                 560

Gly Val Arg Arg Ser Leu Ser Pro Glu Leu Arg Glu Gly Asp Pro Ser
                565                 570                 575

Ser Ser Gln His Leu Pro Ser Thr Pro Ser Ser Pro Arg Val Pro Gly
            580                 585                 590

Ala Leu Ala Ala Ala Lys Ala Ala Lys Tyr Gly Ala Ala Val Pro Gly
            595                 600                 605

Val Leu Gly Gly Leu Gly Ala Leu Gly Gly Val Gly Ile Pro Gly Gly
        610                 615                 620

Val Val Gly Ala Gly Pro Ala Ala Ala Ala Ala Lys Ala Ala
625                 630                 635                 640

Ala Lys Ala Ala Gln Phe Gly Leu Val Gly Ala Ala Gly Leu Gly Gly
                645                 650                 655

Leu Gly Val Gly Gly Leu Gly Val Pro Gly Val Gly Gly Leu Gly Gly
                660                 665                 670

Ile Pro Pro Ala Ala Ala Ala Lys Ala Ala Lys Tyr Gly Ala Ala Gly
            675                 680                 685

Leu Gly Gly Val Leu Gly Gly Ala Gly Gln Phe Pro Leu Gly Gly Val
        690                 695                 700

Ala Ala Arg Pro Gly Phe Gly Leu Ser Pro Ile Phe Pro Gly Gly Ala
705                 710                 715                 720

Cys Leu Gly Lys Ala Cys Gly Arg Lys Arg
                725                 730

<210> SEQ ID NO 2
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Phe Pro Gly Phe Gly Val Gly Val Gly Ile Pro Gly Val Ala Gly
1               5                   10                  15

Val Pro Gly Val Gly Gly Val Pro Gly Val Gly Gly Val Pro Gly Val
                20                  25                  30

Gly Ile Ser Pro Glu Ala Gln Ala Ala Ala Ala Lys Ala Ala Lys
            35                  40                  45

Tyr Gly Val Gly Thr Pro Ala Ala Ala Ala Lys Ala Ala Lys
    50                  55                  60

Ala Ala Gln Phe Gly Leu Val Pro Gly Val Gly Val Ala Pro Gly Val
65                  70                  75                  80

Gly Val Ala Pro Gly Val Gly Val Ala Pro Gly Val Gly Leu Ala Pro
                85                  90                  95

Gly Val Gly Val Ala Pro Gly Val Gly Val Ala Pro Gly Val Gly Val
                100                 105                 110

Ala Pro Ala Ile Gly Pro Glu Ala Gln Ala Ala Ala Ala Lys Ala
            115                 120                 125

Ala Lys Tyr Gly Val Gly Thr Pro Ala Ala Ala Ala Lys Ala Ala
        130                 135                 140

Ala Lys Ala Ala Gln Phe Gly Leu Val Pro Gly Val Gly Val Ala Pro
145                 150                 155                 160

Gly Val Gly Val Ala Pro Gly Val Gly Val Ala Pro Gly Val Gly Leu
                165                 170                 175
```

```
Ala Pro Gly Val Gly Val Ala Pro Gly Val Gly Val Ala Pro Gly Val
            180                 185                 190

Gly Val Ala Pro Ala Ile Gly Pro
        195                 200

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Ala Ala Lys
  1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Ala Ala Ala Lys
  1               5

<210> SEQ ID NO 5
<211> LENGTH: 6
<212> TYPE: PRT
<213> ORGANISM: Homo sapiens

<400> SEQUENCE: 5

Pro Gly Val Gly Val Ala
  1               5

<210> SEQ ID NO 6
<211> LENGTH: 5
<212> TYPE: PRT
<213> ORGANISM: Homo sapiens

<400> SEQUENCE: 6

Val Pro Gly Val Gly
  1               5

<210> SEQ ID NO 7
<211> LENGTH: 4
<212> TYPE: PRT
<213> ORGANISM: Homo sapiens

<400> SEQUENCE: 7

Val Pro Gly Gly
  1

<210> SEQ ID NO 8
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Pro Gly Phe Gly Val Gly Val Gly Gly Ile Pro Gly Val Ala Gly Val
  1               5                  10                  15
```

-continued

Pro Gly Val Gly Gly Val Pro Gly Val Gly Val Pro Gly Val Gly
            20                  25                  30

Ile Ser Pro Glu Ala Gln Ala Ala Ala Ala Lys Ala Ala Lys Tyr
        35                  40                  45

Gly Val Gly Thr Pro Ala Ala Ala Ala Lys Ala Ala Lys Ala
    50                  55                  60

Ala Gln Phe Gly Leu Val Pro Gly Val Gly Val Ala Pro Gly Val Gly
65                  70                  75                  80

Val Ala Pro Gly Val Gly Val Ala Pro Gly Val Gly Leu Ala Pro Gly
                85                  90                  95

Val Gly Val Ala Pro Gly Val Gly Val Ala Pro Gly Val Gly Val Ala
            100                 105                 110

Pro Ala Ile Gly Pro
        115

<210> SEQ ID NO 9
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Phe Pro Gly Phe Gly Val Gly Val Gly Gly Ile Pro Gly Val Ala Gly
1               5                   10                  15

Val Pro Gly Val Gly Gly Val Pro Gly Val Gly Gly Val Pro Gly Val
            20                  25                  30

Gly Ile Ser Pro Glu Ala Gln Ala Ala Ala Ala Lys Ala Ala Lys
        35                  40                  45

Tyr Gly Val Gly Thr Pro Ala Ala Ala Ala Lys Ala Ala Lys
50                  55                  60

Ala Ala Gln Phe Gly Leu Val Pro Gly Val Gly Val Ala Pro Gly Val
65                  70                  75                  80

Gly Val Ala Pro Gly Val Gly Val Ala Pro Gly Val Gly Leu Ala Pro
                85                  90                  95

Gly Val Gly Val Ala Pro Gly Val Gly Val Ala Pro Gly Val Gly Val
            100                 105                 110

Ala Pro Ala Ile Gly Pro
        115

<210> SEQ ID NO 10
<211> LENGTH: 199
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Pro Gly Phe Gly Val Gly Val Gly Gly Ile Pro Gly Val Ala Gly Val
1               5                   10                  15

Pro Gly Val Gly Gly Val Pro Gly Val Gly Gly Val Pro Gly Val Gly
            20                  25                  30

Ile Ser Pro Glu Ala Gln Ala Ala Ala Ala Lys Ala Ala Lys Tyr
        35                  40                  45

Gly Val Gly Thr Pro Ala Ala Ala Ala Lys Ala Ala Lys Ala
    50                  55                  60

Ala Gln Phe Gly Leu Val Pro Gly Val Gly Val Pro Gly Val Gly
65                  70                  75                  80

Val Ala Pro Gly Val Gly Val Ala Pro Gly Val Gly Leu Ala Pro Gly
                85                  90                  95

Val Gly Val Ala Pro Gly Val Gly Val Ala Pro Gly Val Gly Val Ala
            100                 105                 110

Pro Ala Ile Gly Pro Glu Ala Gln Ala Ala Ala Ala Lys Ala Ala
            115                 120                 125

Lys Tyr Gly Val Gly Thr Pro Ala Ala Ala Ala Lys Ala Ala Ala
130                 135                 140

Lys Ala Ala Gln Phe Gly Leu Val Pro Gly Val Gly Val Ala Pro Gly
145                 150                 155                 160

Val Gly Val Ala Pro Gly Val Gly Val Ala Pro Gly Val Gly Leu Ala
            165                 170                 175

Pro Gly Val Gly Val Ala Pro Gly Val Gly Val Ala Pro Gly Val Gly
            180                 185                 190

Val Ala Pro Ala Ile Gly Pro
            195

<210> SEQ ID NO 11
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Phe Pro Gly Phe Gly Val Gly Val Gly Ile Pro Gly Val Ala Gly
1               5                   10                  15

Val Pro Gly Val Gly Gly Val Pro Gly Val Gly Gly Val Pro Gly Val
                20                  25                  30

Gly Ile Ser Pro Glu Ala Gln Ala Ala Ala Ala Lys Ala Ala Lys
            35                  40                  45

Tyr Gly Val Gly Thr Pro Ala Ala Ala Ala Lys Ala Ala Ala Lys
50                  55                  60

Ala Ala Gln Phe Gly Leu Val Pro Gly Val Gly Val Ala Pro Gly Val
65                  70                  75                  80

Gly Val Ala Pro Gly Val Gly Val Ala Pro Gly Val Gly Leu Ala Pro
                85                  90                  95

Gly Val Gly Val Ala Pro Gly Val Gly Val Ala Pro Gly Val Gly Val
            100                 105                 110

Ala Pro Ala Ile Gly Pro Glu Ala Gln Ala Ala Ala Ala Lys Ala
            115                 120                 125

Ala Lys Tyr Gly Val Gly Thr Pro Ala Ala Ala Ala Lys Ala Ala
130                 135                 140

Ala Lys Ala Ala Gln Phe Gly Leu Val Pro Gly Val Gly Val Ala Pro
145                 150                 155                 160

Gly Val Gly Val Ala Pro Gly Val Gly Val Ala Pro Gly Val Gly Leu
            165                 170                 175

Ala Pro Gly Val Gly Val Ala Pro Gly Val Gly Val Ala Pro Gly Val
            180                 185                 190

Gly Val Ala Pro Ala Ile Gly Pro Glu Ala Gln Ala Ala Ala Ala
            195                 200                 205

Lys Ala Ala Lys Tyr Gly Val Gly Thr Pro Ala Ala Ala Ala Lys
210                 215                 220

```
Ala Ala Ala Lys Ala Ala Gln Phe Gly Leu Val Pro Gly Val Gly Val
225                 230                 235                 240

Ala Pro Gly Val Gly Val Ala Pro Gly Val Gly Val Ala Pro Gly Val
            245                 250                 255

Gly Leu Ala Pro Gly Val Gly Val Ala Pro Gly Val Gly Val Ala Pro
        260                 265                 270

Gly Val Gly Val Ala Pro Ala Ile Gly Pro Glu Ala Gln Ala Ala Ala
    275                 280                 285

Ala Ala Lys Ala Ala Lys Tyr Gly Val Gly Thr Pro Ala Ala Ala Ala
    290                 295                 300

Ala Lys Ala Ala Ala Lys Ala Ala Gln Phe Gly Leu Val Pro Gly Val
305                 310                 315                 320

Gly Val Ala Pro Gly Val Gly Val Ala Pro Gly Val Gly Val Ala Pro
            325                 330                 335

Gly Val Gly Leu Ala Pro Gly Val Gly Val Ala Pro Gly Val Gly Val
        340                 345                 350

Ala Pro Gly Val Gly Val Ala Pro Ala Ile Gly Pro
    355                 360

<210> SEQ ID NO 12
<211> LENGTH: 363
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Pro Gly Phe Gly Val Gly Val Gly Ile Pro Gly Val Ala Gly Val
1               5                   10                  15

Pro Gly Val Gly Gly Val Pro Gly Val Gly Val Pro Gly Val Gly
            20                  25                  30

Ile Ser Pro Glu Ala Gln Ala Ala Ala Ala Lys Ala Ala Lys Tyr
            35                  40                  45

Gly Val Gly Thr Pro Ala Ala Ala Ala Lys Ala Ala Lys Ala
    50                  55                  60

Ala Gln Phe Gly Leu Val Pro Gly Val Gly Val Ala Pro Gly Val Gly
65                  70                  75                  80

Val Ala Pro Gly Val Gly Val Ala Pro Gly Val Gly Leu Ala Pro Gly
            85                  90                  95

Val Gly Val Ala Pro Gly Val Gly Val Ala Pro Gly Val Gly Val Ala
            100                 105                 110

Pro Ala Ile Gly Pro Glu Ala Gln Ala Ala Ala Ala Lys Ala Ala
        115                 120                 125

Lys Tyr Gly Val Gly Thr Pro Ala Ala Ala Ala Lys Ala Ala Ala
130                 135                 140

Lys Ala Ala Gln Phe Gly Leu Val Pro Gly Val Gly Val Ala Pro Gly
145                 150                 155                 160

Val Gly Val Ala Pro Gly Val Gly Val Ala Pro Gly Val Gly Leu Ala
            165                 170                 175

Pro Gly Val Gly Val Ala Pro Gly Val Gly Val Ala Pro Gly Val Gly
        180                 185                 190

Val Ala Pro Ala Ile Gly Pro Glu Ala Gln Ala Ala Ala Ala Lys
        195                 200                 205

Ala Ala Lys Tyr Gly Val Gly Thr Pro Ala Ala Ala Ala Lys Ala
    210                 215                 220
```

-continued

```
Ala Ala Lys Ala Ala Gln Phe Gly Leu Val Pro Gly Val Gly Val Ala
225                 230                 235                 240

Pro Gly Val Gly Val Ala Pro Gly Val Gly Val Ala Pro Gly Val Gly
                245                 250                 255

Leu Ala Pro Gly Val Gly Val Ala Pro Gly Val Gly Val Ala Pro Gly
            260                 265                 270

Val Gly Val Ala Pro Ala Ile Gly Pro Glu Ala Gln Ala Ala Ala Ala
        275                 280                 285

Ala Lys Ala Ala Lys Tyr Gly Val Gly Thr Pro Ala Ala Ala Ala Ala
    290                 295                 300

Lys Ala Ala Ala Lys Ala Ala Gln Phe Gly Leu Val Pro Gly Val Gly
305                 310                 315                 320

Val Ala Pro Gly Val Gly Val Ala Pro Gly Val Gly Val Ala Pro Gly
                325                 330                 335

Val Gly Leu Ala Pro Gly Val Gly Val Ala Pro Gly Val Gly Val Ala
            340                 345                 350

Pro Gly Val Gly Val Ala Pro Ala Ile Gly Pro
            355                 360
```